United States Patent
Il et al.

(10) Patent No.: US 9,776,950 B2
(45) Date of Patent: Oct. 3, 2017

(54) ESTER PRODUCTION METHOD AND ESTER PRODUCTION DEVICE

(71) Applicant: UBE INDUSTRIES, LTD., Ube-shi, Yamaguchi (JP)

(72) Inventors: Hirofumi Il, Ube (JP); Yuya Fukui, Ube (JP); Syuji Tanaka, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 0 days.

(21) Appl. No.: 15/323,838

(22) PCT Filed: Jul. 3, 2015

(86) PCT No.: PCT/JP2015/069258
§ 371 (c)(1),
(2) Date: Jan. 4, 2017

(87) PCT Pub. No.: WO2016/002927
PCT Pub. Date: Jan. 7, 2016

(65) Prior Publication Data
US 2017/0158603 A1    Jun. 8, 2017

(30) Foreign Application Priority Data

Jul. 4, 2014    (JP) ................................ 2014-138881

(51) Int. Cl.
C07C 67/36     (2006.01)
B01J 19/00     (2006.01)
B01J 19/24     (2006.01)

(52) U.S. Cl.
CPC ........... *C07C 67/36* (2013.01); *B01J 19/0006* (2013.01); *B01J 19/245* (2013.01); *B01J 2219/00164* (2013.01); *B01J 2219/24* (2013.01)

(58) Field of Classification Search
CPC ..... C07C 67/36; B01J 19/0006; B01J 19/245; B01J 2219/00164; B01J 2219/24
USPC ......................................................... 558/260
See application file for complete search history.

(56) References Cited

FOREIGN PATENT DOCUMENTS

| CN | 102019164 A | 4/2011 |
|---|---|---|
| JP | H11-246477 A | 9/1999 |
| JP | H11-279116 A | 10/1999 |
| JP | 2004-091484 A | 3/2004 |
| JP | 2004-107336 A | 4/2004 |
| JP | 2004-323470 A | 11/2004 |
| JP | 2011-236208 A | 11/2011 |
| JP | 2013-528572 A | 7/2013 |
| WO | 2011/127752 A1 | 10/2011 |
| WO | 2013/150840 A1 | 10/2013 |

OTHER PUBLICATIONS

Sep. 29, 2015 Search Report issued in International Patent Application No. PCT/JP2015/069258.

*Primary Examiner* — Kristin Vajda
(74) *Attorney, Agent, or Firm* — Oliff PLC

(57) ABSTRACT

Provided is a production device including: a first reactor to form a second gas containing an ester and nitric oxide from a first gas containing carbon monoxide, a nitrite, and nitric oxide; an absorption column to separate the second gas and an absorbing solution into a condensate containing the ester and a noncondensable gas; a second reactor to introduce an alcohol, the noncondensable gas, and oxygen gas thereinto to form a third gas containing nitric oxide and a nitrite; a third reactor to form a fourth gas containing a nitrite from the noncondensable gas and a bottom liquid from the second reactor and to feed the fourth gas to the second reactor; a first measurement unit to measure the concentration of a nitrite in the first gas; and a first flow rate-adjusting unit to adjust the amount of the noncondensable gas to the third reactor based on the concentration.

20 Claims, 19 Drawing Sheets

ESTER PRODUCTION METHOD AND ESTER PRODUCTION DEVICE

TECHNICAL FIELD

The present disclosure relates to an ester production method and an ester production device.

BACKGROUND ART

Carbonate esters are useful compounds as a raw material for synthesis of aromatic polycarbonates, and drugs and agricultural chemicals, etc. Oxalic esters are also useful compounds as a raw material for synthesis of glycols, dye intermediates, and drugs, etc. Methods for continuous mass production of these compounds have been previously proposed.

As a process to continuously produce a carbonate ester, a process is known in which synthesis through gas phase reaction is performed by using carbon monoxide and a nitrite ester in the presence of a solid catalyst of a platinum group metal (e.g., see Patent Literature 1). In such a process, a carbonate ester can be obtained through the following reaction formula (i).

$$CO + 2RONO \rightarrow ROC(=O)OR + 2NO \quad (i)$$

NO obtained through the reaction represented by the formula (i) reacts with an alcohol in accordance with the following formula (ii) to form a nitrite ester in a reaction column (regeneration column). By reusing the nitrite ester obtained in the reaction and newly feeding carbon monoxide, a carbonate ester can be continuously produced. An oxalic ester can be also produced continuously in a similar process (e.g., see Patent Literature 2). Thus, carbonate esters and oxalic esters are produced by circulating nitrogen components such as a nitrite ester.

$$2NO + \tfrac{1}{2}O_2 + 2ROH \rightarrow 2RONO + H_2O \quad (ii)$$

In the process as described above, a reaction represented by the formula (iii) also proceeds in a reaction column. $HNO_3$ formed in the reaction is extracted from the bottom of a reaction column. Patent Literature 3 proposes to introduce $HNO_3$ thus formed into a nitric acid-concentrating column for effective use of nitric acid to reduce loss of nitrogen components.

$$NO + \tfrac{3}{4}O_2 + \tfrac{1}{2}H_2O \rightarrow HNO_3 \quad (iii)$$

CITATION LIST

Patent Literature

Patent Literature 1: Japanese Unexamined Patent Publication No. 2004-323470
Patent Literature 2: Japanese Unexamined Patent Publication No. H11-279116
Patent Literature 3: International Publication No. WO2013/150840

SUMMARY OF INVENTION

Technical Problem

In the production methods described in the above Patent Literatures, a desired compound is produced through catalytic reaction while a nitrite ester is regenerated. Although such production methods enable mass production through scaling-up, it is required to establish a technique to continue production stably and efficiently. The reason is that, once continuous production is interrupted, cumbersome operation of an apparatus such as start-up operation and shutdown operation are required and in addition loss of opportunity due to the shutdown increases.

To continue production stably, it is required to continue operation stably while the activity of a catalyst in a reactor is maintained. In such a reaction with a catalyst, the reaction rate decreases as the concentration of a component to react becomes excessively low to thereby decrease the production of an intended product. If the concentration of a nitrite ester in raw materials becomes excessively low, for example, the production of an ester including at least one of a carbonate ester and an oxalic ester, as an intended product, decreases. If the concentration of a nitrite ester becomes excessively high, on the other hand, safety in operation is expected to be deteriorated. Accordingly, it is required to suppress the variation of the composition of raw materials to be fed to a reactor.

In view of this, an object of the present invention is to provide, in one aspect, a production method enabling stable production of an ester including at least one of a carbonate ester and an oxalic ester. In another aspect, an object of the present invention is to provide a production device enabling stable production of an ester including at least one of a carbonate ester and an oxalic ester.

Solution to Problem

The present invention provides, in one aspect, a method for producing an ester including at least one of a carbonate ester and an oxalic ester, the method comprising:
introducing a first gas containing carbon monoxide, a nitrite ester, and nitric oxide into a first reactor and reacting the first gas in the presence of a catalyst to obtain a second gas containing an ester including at least one of a carbonate ester and an oxalic ester and nitric oxide;
allowing the second gas to contact with an absorbing solution to obtain a condensate containing the ester and a noncondensable gas containing nitric oxide;
introducing an alcohol and a mixed gas obtained by mixing the noncondensable gas with oxygen gas into a second reactor to obtain a third gas containing a nitrite ester and nitric oxide;
distilling the condensate to obtain the ester;
mixing the third gas with carbon monoxide to obtain the first gas;
feeding the noncondensable gas and a bottom liquid discharged from the bottom of the second reactor and containing water, nitric acid, and an alcohol to a third reactor to form a fourth gas containing a nitrite ester, and feeding the fourth gas to the second reactor; and
measuring the concentration of a nitrite ester in the first gas and/or the third gas, and at least one of adjusting the amount of the noncondensable gas to feed to the third reactor on the basis of the concentration and adjusting the amount of nitric acid to feed to the third reactor on the basis of the concentration.

The production method includes obtaining a second gas containing an ester including at least one of a carbonate ester and an oxalic ester and nitric oxide from a first gas obtained by mixing a third gas containing nitric oxide and a nitrite ester with carbon monoxide by using a catalyst in a first reactor. Further, the production method includes measuring the concentration of a nitrite ester in the first gas and/or the third gas, and at least one of adjusting the amount of the noncondensable gas to feed to the third reactor on the basis of the concentration and adjusting the amount of nitric acid to feed to the third reactor on the basis of the concentration. These steps enable adjustment of the amount of a nitrite ester to be formed in the third reactor. By virtue of this, the variation of the concentration of a nitrite ester in the first gas and/or the third gas can be sufficiently reduced. Accordingly, lowering of the reaction rate in the first reactor is suppressed and at least one of a carbonate ester and an oxalic ester can be thus efficiently formed. In addition, the concentration of a nitrite ester in the first gas and the third gas is suppressed from excessively increasing and the safety can be thus enhanced.

The present invention provides, in another aspect, a method for producing an ester including at least one of a carbonate ester and an oxalic ester, the method comprising:

introducing a first gas containing carbon monoxide, a nitrite ester, and nitric oxide into a first reactor and reacting the first gas in the presence of a catalyst to obtain a second gas containing an ester including at least one of a carbonate ester and an oxalic ester and nitric oxide;

allowing the second gas to contact with an absorbing solution to obtain a condensate containing the ester and a noncondensable gas containing nitric oxide;

introducing an alcohol and a mixed gas obtained by mixing the noncondensable gas with oxygen gas into a second reactor to obtain a third gas containing a nitrite ester and nitric oxide;

distilling the condensate to obtain the ester;

mixing the third gas with carbon monoxide to obtain the first gas; and measuring the concentration of a nitrite ester in the first gas and/or the third gas and adjusting the amount of nitric oxide to mix with the noncondensable gas on the basis of the concentration.

In the production method, a second gas containing at least one of a carbonate ester and an oxalic ester and nitric oxide is formed from a first gas obtained by mixing a third gas containing nitric oxide and a nitrite ester with carbon monoxide by using the catalyst in the first reactor. Then, the concentration of a nitrite ester in the first gas and/or the third gas is measured to adjust the amount of nitric oxide to mix with the noncondensable gas on the basis of the concentration. This enables adjustment of the amount of a nitrite ester to be formed in the second reactor. By virtue of this, the variation of the concentration of a nitrite ester in the first gas and/or the third gas can be sufficiently reduced. Accordingly, lowering of the reaction rate in the first reactor is suppressed and at least one of a carbonate ester and an oxalic ester can be thus efficiently formed. In addition, the concentration of a nitrite ester in the first gas and the third gas is suppressed from excessively increasing and the safety can be thus enhanced.

In some embodiments, the concentration of a nitrite ester in the first gas and/or the third gas may be measured by using non-dispersive infrared analysis. Non-dispersive infrared analysis enables measurement of the concentration of a nitrite ester quicker than other analytical methods such as gas chromatography. By virtue of this, adjustment of the amount of the noncondensable gas to feed to the third reactor and/or adjustment of the amount of nitric oxide to feed for mixing with the noncondensable gas can be performed quickly. Accordingly, the variation of the concentration of a nitrite ester in the first gas can be further reduced.

In the non-dispersive infrared analysis, an infrared analyzer including a measurement cell to allow the first gas and/or the third gas to flow therethrough and a detector encapsulating ammonia may be used to measure the concentration of a nitrite ester in the first gas and/or the third gas. Ammonia has absorption peaks in the same wavenumber regions as wavenumber regions including the infrared absorption peaks of a nitrite ester. In addition, ammonia is safer than nitrite esters. Thus, use of a detector encapsulating ammonia enables measurement of the concentration of a nitrite ester at a high precision concomitantly with enhancement of safety.

In some embodiments, the production method may comprise measuring the concentration of nitric oxide in the first gas and/or the third gas and adjusting the amount of oxygen gas to mix with the noncondensable gas on the basis of the concentration. Because nitric oxide does not have an adverse effect on the activity of the catalyst in the first reactor, nitric oxide can be present in the first gas and the third gas at a concentration higher than that of oxygen gas. Thus, the concentration of nitric oxide in the first gas and the third gas can be detected at a higher precision than the concentration of (molecular) oxygen. In addition, the concentration of nitric oxide and the concentration of oxygen in the first gas and the third gas are closely related. Thus, the concentration of oxygen in the first gas can be monitored at a high precision by measuring the concentration of nitric oxide without directly measuring the concentration of oxygen in each of the first gas and the third gas. By virtue of this, lowering of the activity of the catalyst and deterioration of the catalyst caused by oxygen gas can be further suppressed.

In the production method, the concentration of a nitrite ester in the first gas may be maintained at 5 to 25% by volume based on the total of the first gas. This enables sufficient utilization of the activity of the catalyst to efficiently produce at least one of a carbonate ester and an oxalic ester in combination with sufficient enhancement of the safety.

In the production method, the concentration of a nitrite ester in the third gas may be maintained, for example, at 5 to 30% by volume based on the total of the third gas. This enables sufficient utilization of the activity of the catalyst to efficiently produce at least one of a carbonate ester and an oxalic ester in combination with sufficient enhancement of the safety.

The present invention provides, in still another aspect, a device for producing an ester including at least one of a carbonate ester and an oxalic ester, the device comprising:

a first reactor to react a first gas containing carbon monoxide, a nitrite ester, and nitric oxide in the presence of a catalyst to obtain a second gas containing an ester including at least one of a carbonate ester and an oxalic ester and nitric oxide;

an absorption column to allow the second gas to contact with an absorbing solution to separate into a condensate containing the ester and a noncondensable gas containing nitric oxide;

a second reactor to introduce an alcohol and a mixed gas containing the noncondensable gas and oxygen gas thereinto to obtain a third gas containing a nitrite ester and nitric oxide;

a distillation column to distill the condensate to obtain the ester;

a junction part to allow the third gas and carbon monoxide to join together to obtain the first gas;

a third reactor to form a fourth gas containing a nitrite ester from the noncondensable gas and a bottom liquid discharged from the bottom of the second reactor and containing water, nitric acid, and an alcohol and to feed the fourth gas to the second reactor;

a first measurement unit to measure the concentration of a nitrite ester in the first gas and/or the third gas; and at least one of a first flow rate-adjusting unit to adjust the amount of the noncondensable gas to feed to the third reactor on the basis of the concentration, and a second flow rate-adjusting unit to adjust the amount of nitric acid to feed to the third reactor on the basis of the concentration.

The production device comprises a first reactor including a catalyst. In the first reactor, a second gas containing at least one of a carbonate ester and an oxalic ester and nitric oxide is obtained from a first gas obtained by allowing a third gas containing nitric oxide and a nitrite ester and carbon monoxide to join together. Further, the production device comprises a first measurement unit to measure the concentration of a nitrite ester in the first gas and/or the third gas, and at least one of a first flow rate-adjusting unit to adjust the amount of the noncondensable gas to feed to the third reactor on the basis of the concentration and a second flow rate-adjusting unit to adjust the amount of nitric acid to feed to the third reactor on the basis of the concentration.

This enables adjustment of the amount of a nitrite ester to be formed in the third reactor. By virtue this, the variation of the concentration of a nitrite ester in the first gas and/or the third gas can be sufficiently reduced. Accordingly, lowering of the reaction rate in the first reactor is suppressed and at least one of a carbonate ester and an oxalic ester can be thus efficiently formed. In addition, the concentration of a nitrite ester in the first gas and the third gas is suppressed from excessively increasing and the safety can be thus enhanced.

The present invention provides, in still another aspect, a device for producing an ester including at least one of a carbonate ester and an oxalic ester, the device comprising:

a first reactor to react a first gas containing carbon monoxide, a nitrite ester, and nitric oxide in the presence of a catalyst to obtain a second gas containing an ester including at least one of a carbonate ester and an oxalic ester and nitric oxide;

an absorption column to allow the second gas to contact with an absorbing solution to separate into a condensate containing the ester and a noncondensable gas containing nitric oxide;

a second reactor to introduce an alcohol and a mixed gas containing the noncondensable gas and oxygen gas thereinto to form a third gas containing a nitrite ester and nitric oxide;

a distillation column to distill the condensate to obtain the ester;

a junction part to allow the third gas and carbon monoxide to join together to obtain the first gas;

a first measurement unit to measure the concentration of a nitrite ester in the first gas and/or the third gas; and a third flow rate-adjusting unit to adjust the amount of nitric oxide to mix with the noncondensable gas on the basis of the concentration.

The production device comprises a first reactor including a catalyst. In the first reactor, a second gas containing at least one of a carbonate ester and an oxalic ester and nitric oxide is formed from a first gas obtained by allowing a third gas containing nitric oxide and a nitrite ester and carbon monoxide to join together. Further, the production device comprises a first measurement unit to measure the concentration of a nitrite ester in the first gas and/or the third gas, and a first flow rate-adjusting unit to adjust the amount of nitric oxide to mix with the noncondensable gas on the basis of the concentration. This enables adjustment of the amount of a nitrite ester to be formed in the second reactor. By virtue of this, the variation of the concentration of a nitrite ester in the first gas and/or the third gas can be sufficiently reduced. Accordingly, lowering of the reaction rate in the first reactor is suppressed and at least one of a carbonate ester and an oxalic ester can be thus efficiently formed. In addition, the concentration of a nitrite ester in the first gas and the third gas is suppressed from excessively increasing and the safety can be thus enhanced.

In some embodiments, the production device may comprise a control unit to control at least one of the first flow rate-adjusting unit, the second flow rate-adjusting unit, and the third flow rate-adjusting unit so that the concentration of a nitrite ester in the first gas becomes 5 to 25% by volume based on the total of the first gas. This enables sufficient utilization of the activity of the catalyst to efficiently produce at least one of a carbonate ester and an oxalic ester in combination with sufficient enhancement of the safety. In some other embodiments, the production device may comprise a control unit to control at least one of the first flow rate-adjusting unit, the second flow rate-adjusting unit, and the third flow rate-adjusting unit so that the concentration of a nitrite ester in the third gas becomes 5 to 30% by volume based on the total of the third gas. This enables sufficient utilization of the activity of the catalyst to efficiently produce at least one of a carbonate ester and an oxalic ester in combination with sufficient enhancement of the safety.

The first measurement unit may be a non-dispersive infrared analyzer. A non-dispersive infrared analyzer can measure the concentration of a nitrite ester quicker than other analyzers such as gas chromatographs. Measurement of the concentration of a nitrite ester with a non-dispersive infrared analyzer enables quick adjustment with the flow rate-adjusting unit. Accordingly, the variation of the concentration of a nitrite ester in the first gas can be further reduced.

The non-dispersive infrared analyzer may include a measurement cell to allow the first gas and/or the third gas to flow therethrough and a detector encapsulating ammonia, and may be configured to measure the concentration of a nitrite ester in the first gas and/or the third gas in the measurement cell. Ammonia is safer than nitrite esters as a subject to be measured. Ammonia has absorption peaks in the same wavenumber regions as wavenumber regions including the infrared absorption peaks of a nitrite ester. Thus, use of a detector encapsulating ammonia enables measurement of the concentration of a nitrite ester at a high precision concomitantly with enhancement of safety.

In some embodiments, the production device may comprise: a second measurement unit to measure the concentration of nitric oxide in the first gas and/or the third gas; and a fourth flow rate-adjusting unit to adjust the amount of oxygen gas to mix with the noncondensable gas on the basis of the concentration. Because nitric oxide does not have an adverse effect on the activity of the catalyst in the first reactor, nitric oxide can be present in the first gas and the third gas at a concentration higher than that of oxygen. Thus, the concentration of nitric oxide in the first gas and the third gas can be measured at a higher precision than the concentration of oxygen gas. In addition, the concentration of nitric oxide and the concentration of (molecular) oxygen in the first gas and the third gas are closely related. Thus, the concentration of oxygen in the first gas can be monitored at a high precision by providing the second measurement unit to measure the concentration of nitric oxide without directly measuring the concentration of oxygen in each of the first gas and the third gas. By virtue of this, lowering of the activity of the catalyst and deterioration of the catalyst caused by oxygen gas can be further suppressed.

Advantageous Effects of Invention

The present invention can provide, in one aspect, a production method enabling stable production of an ester including at least one of a carbonate ester and an oxalic ester. In addition, the present invention can provide, in another aspect, a production device enabling stable production of an ester including at least one of a carbonate ester and an oxalic ester.

DESCRIPTION OF EMBODIMENTS

Now, some embodiments of the present invention will be described occasionally with reference to drawings. However, these embodiments in the following are examples to describe the present invention, and are not intended to limit the present invention to the following contents. In the description, an identical sign is used for identical elements or elements having an identical function, and redundant descriptions are occasionally omitted. Positional relation such as up and down and left and right is based on positional relation as shown in a drawing unless otherwise specified. In addition, the dimensional ratio of a drawing is not limited to the ratio as illustrated.

Figure 1:
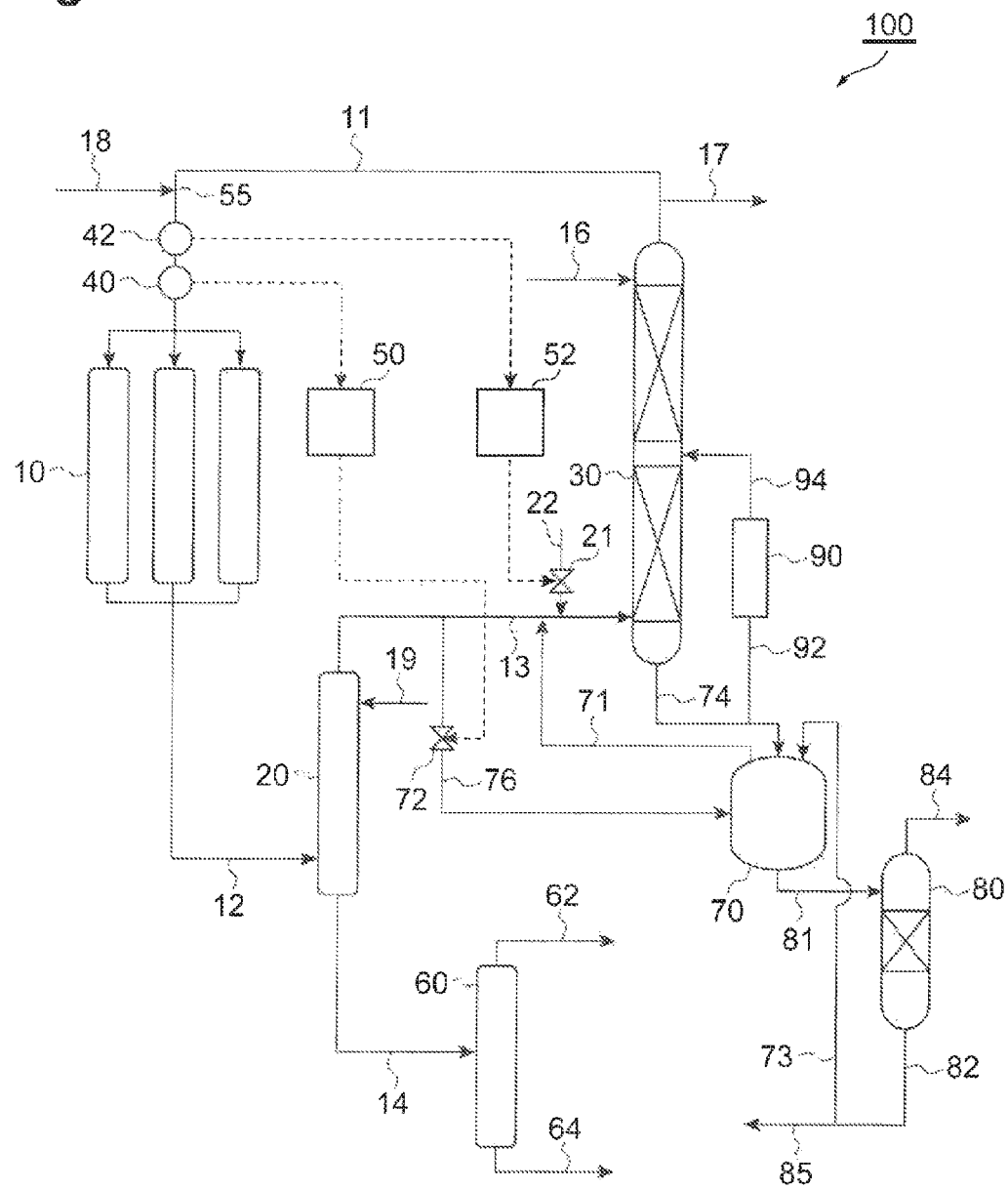
FIG. 1 schematically illustrates an ester production device according to one embodiment.

FIG. 1 schematically illustrates an ester production device according to one embodiment, where the ester contains a carbonate ester and/or an oxalic ester. A production device 100 includes: a first reactor 10 which includes a catalyst to react carbon monoxide and a nitrite ester to form a carbonate ester and/or an oxalic ester and nitric oxide and in which a second gas containing a carbonate ester and/or an oxalic ester and nitric oxide is formed from a first gas containing carbon monoxide, a nitrite ester, and nitric oxide; an absorption column 20 to allow the second gas to contact with an absorbing solution which absorbs a carbonate ester and/or an oxalic ester to separate into a condensate containing a carbonate ester and/or an oxalic ester and a noncondensable gas containing nitric oxide; a second reactor 30 to introduce an alcohol and a mixed gas of the noncondensable gas and oxygen gas thereinto and to react nitric oxide, oxygen, and the alcohol to form a third gas containing a nitrite ester and nitric oxide; and a junction part 55 to allow the third gas and carbon monoxide to join together to obtain the first gas.

The first gas obtained in the junction part 55 is fed to the first reactor 10. In this way, the production device 100 circulates nitrogen components while continuously feeding CO as a raw material to continuously produce an ester including a carbonate ester and/or an oxalic ester as an intended product. The nitrogen components such as NO and a nitrite ester are reused while circulating in the production device 100. The bottom liquid discharged from the bottom of the second reactor 30 contains nitric acid, an alcohol, etc., in addition to water. In view of this, the production device 100 includes a third reactor 70 to form a nitrite ester from the noncondensable gas and the bottom liquid fed from the bottom of the second reactor 30 and containing water, nitric acid, and an alcohol. "Ester" herein encompasses a carbonate ester, an oxalic ester, and a mixture of a carbonate ester and an oxalic ester.

The production device 100 includes: a first measurement unit 40 to measure the concentration of a nitrite ester in the first gas; a first flow rate-adjusting unit 72 to adjust the amount of the noncondensable gas to feed to the third reactor 70; and a control unit 50 configured to determine whether adjustment with the first flow rate-adjusting unit 72 is needed on the basis of a measurement result of the first measurement unit 40 and adjust the flow rate of the noncondensable gas with the first flow rate-adjusting unit 72, as necessary. In addition, the production device 100 includes: a second measurement unit 42 to measure the concentration of nitric oxide in the first gas; a fourth flow rate-adjusting unit 21 to adjust the amount of oxygen gas to mix with the noncondensable gas; and a control unit 52 configured to determine whether adjustment with the fourth flow rate-adjusting unit 21 is needed on the basis of a measurement result of the second measurement unit 42 and adjust the amount of oxygen gas with the fourth flow rate-adjusting unit 21, as necessary.

The first reactor 10 includes a catalyst to react carbon monoxide and a nitrite ester to form a carbonate ester and/or an oxalic ester and nitric oxide. Examples of such catalysts for production of a carbonate ester and/or an oxalic ester include solid catalysts in which a platinum group metal or a compound thereof is supported on a support. The amount of the platinum group metal or compound thereof supported in a solid catalyst is 0.1 to 10% by weight, preferably 0.5 to 2% by weight based on the amount of a support. Examples of the support include inert supports such as activated carbon, alumina (e.g., γ-alumina), zeolite, a molecular sieve, and spinel (e.g., lithium aluminate spinel). The platinum group metal or compound thereof is supported on the support by using a known method such as an impregnation method and an evaporation-to-dryness method.

Examples of the platinum group metal or compound thereof include platinum metal, palladium metal, rhodium metal, and iridium metal. Examples of compounds of platinum group metals include inorganic acid salts (e.g., nitrate, sulfate, phosphate), halides (e.g., chloride, bromide), organic acid salts (e.g., acetate, oxalate, benzoate), and complexes (e.g., lithium tetrachloropalladate, sodium tetrachloropalladate) of these metals. Among them, palladium chloride and a chlorine-containing complex of palladium are preferred. The amount of the platinum group metal or compound thereof supported on the support is preferably 0.01 to 10% by weight, and more preferably 0.2 to 2% by weight.

In addition to the platinum group metal or compound thereof, copper, iron, or bismuth, or a compound thereof may be contained in the catalyst for production of a carbonate ester. Among them, chlorides (e.g., cuprous chloride, cupric chloride, ferrous chloride, ferric chloride, bismuth chloride) are preferred. The amount of them supported on the support is preferably 1:0.1 to 1:50, and more preferably 1:1 to 1:10 in terms of "platinum group metal or compound thereof":"copper, iron, or bismuth, or compound thereof" (mole ratio of metal atoms).

In addition to the platinum group metal or compound thereof, iron or a compound thereof may be contained in the catalyst for production of an oxalic ester. Specific examples of iron or compounds thereof include metal iron, iron (II) compounds (e.g., ferrous sulfate, ferrous nitrate, ferrous chloride, ammonium ferrous sulfate, ferrous lactate, ferrous hydroxide), and iron (III) compounds (e.g., ferric sulfate, ferric nitrate, ferric chloride, ammonium ferric sulfate, ferric lactate, ferric hydroxide, ferric citrate). The amount of the iron or compound thereof supported on the support is preferably 10000:1 to 1:4, and more preferably 5000:1 to 1:3 in terms of "platinum group metal or compound thereof": "iron or compound thereof" (mole ratio of metal atoms).

The method for preparing the catalyst is not particularly limited, and for example, the catalyst may be prepared by allowing the platinum group compound to be supported on the support by using a known method such as an impregnation method and an evaporation-to-dryness method followed by drying the support.

In the case that a carbonate ester is produced, a first gas containing carbon monoxide, a nitrite ester, and nitric oxide is introduced into a first reactor 10 including the catalyst for production of a carbonate ester. Thereby, a gas phase reaction represented by the following formula (1) proceeds. In the formula (1), R denotes an alkyl group. R is preferably a $C_{1-3}$ alkyl group.

CO+2RONO→ROC(=O)OR+2NO     (1)

In the case that an oxalic ester is produced, a first gas containing carbon monoxide, a nitrite ester, and nitric oxide is introduced into a first reactor 10 including the catalyst for production of an oxalic ester. Thereby, a gas phase reaction represented by the following formula (2) proceeds. In the formula (2), R denotes an alkyl group. R is preferably a $C_{1-3}$ alkyl group.

2CO+2RONO→(RCO$_2$)$_2$+2NO     (2)

The content of a nitrite ester in the first gas may be, for example, 5 to 25% by volume, or 10 to 25% by volume, or 10 to 20% by volume based on the total of the first gas. "% by volume" herein refers to a volume fraction at the standard state (25° C., 100 kPa).

The content of nitric oxide in the first gas is, for example, 1 to 20% by volume based on the total of the first gas. The content of carbon monoxide in the first gas is, for example, 10 to 40% by volume based on the total of the first gas. The first gas may contain an inert gas in combination with carbon monoxide, a nitrite ester, and nitric oxide.

In the present embodiment, three first reactors 10 are included. A plurality of first reactors 10 may be included as in the present embodiment, or one first reactor may be included in some other embodiments. The production of a carbonate ester and/or an oxalic ester can increase by including a plurality of first reactors 10 as in the present embodiment. A plurality of first reactors 10 may be used simultaneously to increase the production of a carbonate ester and/or an oxalic ester. A plurality of first reactors 10 may be used not simultaneously but alternately or sequentially so that operation of the production device 100 for a carbonate ester and/or an oxalic ester can be continued during exchange of the catalyst or maintenance for the first reactors 10.

In the first reactor 10, a second gas containing a carbonate ester and/or an oxalic ester and nitric oxide is formed through the reaction(s) represented by the above formula (1) and/or formula (2). The concentration of a carbonate ester and/or an oxalic ester in the second gas is, for example, 1 to 50% by volume based on the total of the second gas. The concentration of nitric oxide in the second gas is, for example, 1 to 20% by volume based on the total of the second gas. The second gas may contain unreacted carbon monoxide. The concentration of carbon monoxide in the second gas is, for example, 1 to 20% by volume.

The second gas formed in the first reactor 10 passes through a passage 12 to be introduced into an absorption column 20. The absorption column 20 is only required to be a column capable of bringing into gas-liquid contact, and examples thereof include plate absorption columns such as sieve tray, bubble cap tray, and bubble tray absorption columns, and packed absorption columns packed with an irregular-shaped packing material such as a Pall ring and a Raschig ring, or a regular-shaped packing material such as a sheet-like plate, a gauze-like plate, and a composite plate including them in combination.

The second gas introduced to the lower part of the absorption column 20 from the first reactor 10 through the passage 12 is brought into countercurrent contact with an absorbing solution for absorption of a carbonate ester and/or an oxalic ester (hereinafter, simply referred to as "absorbing solution") introduced to the upper part of the absorption column 20 from a passage 19. In this way, the second gas and the absorbing solution are brought into gas-liquid contact to allow at least a part of the carbonate ester and/or oxalic ester contained in the second gas to be absorbed in the absorbing solution. As a result, a condensate containing a carbonate ester and/or an oxalic ester and the absorbing solution and a noncondensable gas containing nitric oxide are obtained.

Examples of the absorbing solution to be used in the absorption column 20 include alcohols, carbonate esters and oxalic esters which have an alkyl group identical to the alkyl group of the carbonate ester and/or oxalic ester.

The amount of the absorbing solution to feed to the absorption column 20 is, for example, 1 to 30% based on the mass of a carbonate ester and/or an oxalic ester in the second gas. Examples of the alcohol include $C_{1-3}$ aliphatic alcohols such as methanol and ethanol. In view of easiness in recovery, alcohols having an alkyl group identical to the alkyl group of a nitrite ester introduced into the first reactor 10 together with carbon monoxide are preferred.

The condensate obtained in the absorption column 20 and containing the absorbing solution and a carbonate ester and/or an oxalic ester is extracted from a passage 14 linked to the bottom of the absorption column 20. The condensate passes through the passage 14 to be introduced into a distillation column 60. In the distillation column 60, the condensate is separated into the absorbing solution and a carbonate ester and/or an oxalic ester by difference in boiling point. In the case that an alcohol with low boiling point such as methanol and ethanol is used for the absorbing solution, the alcohol is discharged from a passage 62 linked to the top of the distillation column 60. From a passage 64 linked to the bottom of the distillation column 60, a carbonate ester and/or an oxalic ester is discharged. A distillation column may be further provided in the downstream side of the passage 64 to separate a carbonate ester and an oxalic ester by difference in boiling point. Alternatively, a passage may be further linked to the distillation column 60 to separate the absorbing solution, a carbonate ester, and an oxalic ester simultaneously.

Among carbonate esters, dimethyl carbonate forms an azeotrope with methanol at the azeotropic point. In this case, it is difficult to separate the components by using a simple distillation process. Thus, dimethyl carbonate can be isolated by performing pressure distillation or adding another component to prevent the occurrence of azeotropy.

On the other hand, the noncondensable gas obtained in the absorption column 20 and containing nitric oxide is extracted from a passage 13 linked to the upper part of the absorption column 20 and flows through the passage 13 to a second reactor 30. The noncondensable gas may contain carbon monoxide. To the passage 13, a passage 76 to feed the noncondensable gas to a third reactor 70 and a passage 22 to introduce oxygen gas are linked in the order presented from the upstream side.

The oxygen gas fed from the passage 22 is mixed with the noncondensable gas to form a mixed gas. The mixed gas containing the noncondensable gas and oxygen gas passes through the passage 13 to be introduced into the second reactor 30. The passage 22 is provided with a fourth flow rate-adjusting unit 21 to adjust the amount of oxygen gas to introduce to the passage 13. For example, a flow regulating valve can be used for the fourth flow rate-adjusting unit 21. The fraction of oxygen gas in the mixed gas can be adjusted by adjusting the degree of opening of the flow regulating valve.

The mixed gas after passing through the passage 13 is introduced into the second reactor 30 from the lower side, and then brought into countercurrent contact with an alcohol (ROH) introduced from a passage 16 linked to the upper side of the second reactor 30, and a reaction represented by the following formula (3) proceeds. Through the reaction, a nitrite ester (RONO) is formed. In the formula (3), R denotes an alkyl group. R is preferably a $C_{1-3}$ alkyl group. In the entire of the production device 100, the second reactor 30 and the third reactor 70 have a function to regenerate a nitrite ester.

In the second reactor 30, a side reaction represented by the formula (4) may proceed. In view of enhancing the efficiency of the entire of equipment, it is preferable to allow the reaction represented by the formula (3) to proceed, rather than the formula (4). It is preferable to set the mixing ratio between nitric oxide and oxygen in the mixed gas to a ratio of 0.08 to 0.2 mol per mole of nitric oxide contained in the mixed gas. Mixing oxygen gas and the noncondensable gas so as to reach such a ratio can prevent unreacted oxygen gas from flowing into the first reactor 10 and can prevent the reaction represented by the formula (4) from proceeding. In addition to this, the reaction represented by the formula (3) can be accelerated. Thus, a nitrite ester can be efficiently regenerated.

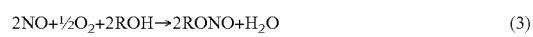
$$2NO+\tfrac{1}{2}O_2+2ROH \rightarrow 2RONO+H_2O \qquad (3)$$

$$NO+\tfrac{3}{4}O_2+\tfrac{1}{2}H_2O \rightarrow HNO_3 \qquad (4)$$

For the alcohol introduced from the passage 16, an alcohol having an alkyl group constituting a carbonate ester and/or an oxalic ester to be produced in the production device 100 is used. $C_{1-3}$ aliphatic alcohols such as methanol and ethanol are preferred for such an alcohol. In view of allowing the reaction represented by the formula (3) to proceed sufficiently, it is preferable to set the amount of an alcohol to feed to the second reactor 30 to 0.5 to 1.5 in a mole ratio to the amount of nitric oxide contained in the mixed gas to feed.

The reaction temperature in the second reactor 30 can be appropriately set in accordance with the type of an alcohol introduced from the passage 16. In the case that methanol is used for the alcohol, the reaction temperature is, for example, 0 to 80° C., the reaction pressure is, for example, 0.1 to 1 MPa, and the duration for gas-liquid contact is, for example, 0.5 to 30 seconds.

The third gas extracted from the upper part of the second reactor 30 contains nitric oxide and trace components such as nitrous oxide and carbon dioxide in addition to a nitrite ester formed through the reaction represented by the formula (3). These trace components can be appropriately discharged to the outside of the system as an off-gas through a passage 17 branching from a passage 11.

The content of a nitrite ester in the third gas may be, for example, 5 to 30% by volume, or may be 15 to 30% by volume based on the total of the third gas. If the content of a nitrite ester is less than 5% by volume, the reaction represented by the above formula (1) does not proceed sufficiently in the first reactor 10, and the yield of a carbonate ester and/or an oxalic ester tends to be lowered. If the content of a nitrite ester is more than 30% by volume, on the other hand, the safety tends to be lowered.

The content of nitric oxide in the third gas is, for example, 1 to 25% by volume based on the total of the third gas. The third gas may contain an inert gas in combination with carbon monoxide, a nitrite ester, and nitric oxide.

A bottom liquid containing water and nitric acid which are formed through the reactions represented by the formula (3) and the formula (4) and an unreacted alcohol is extracted from a passage 74 linked to the bottom of the second reactor 30. The bottom liquid flows through the passage 74 to be fed to the third reactor 70. To the third reactor 70, the noncondensable gas after flowing through the passage 76 is fed.

In the third reactor 70, the noncondensable gas and the bottom liquid are brought into contact and, for example, reactions represented by the formulas (5) and (6) proceed to form a nitrite ester. Specifically, nitric acid and an alcohol contained in the bottom liquid and carbon monoxide and/or nitric oxide contained in the noncondensable gas react together to form a nitrite ester. Here, R in the formulas (5) and (6) denotes an alkyl group.

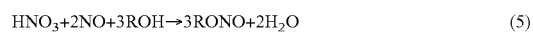
$$HNO_3+2NO+3ROH \rightarrow 3RONO+2H_2O \qquad (5)$$

$$HNO_3+CO+ROH \rightarrow RONO+H_2O+CO_2 \qquad (6)$$

As a result of the above-mentioned reactions, a fourth gas containing a nitrite ester is discharged from the upper part of the third reactor 70. The concentration of a nitrite ester in the fourth gas is, for example, 1 to 25% by volume. The fourth gas flows through a passage 71 and joins the noncondensable gas flowing through the passage 13, and is then fed to the second reactor 30.

A nitrite ester formed in the third reactor 70 is contained in the third gas discharged from the upper part of the second reactor 30, together with a nitrite ester formed in the second reactor 30. In the above formula (3), 1 mol of a nitrite ester is obtained from 1 mol of nitric oxide, and in the above formula (5), in contrast, 1.5 mol of a nitrite ester is obtained from 1 mol of nitric oxide. Accordingly, the concentration of a nitrite ester in the first gas and the third gas can be increased through increasing the amount of the noncondensable gas to feed to the third reactor 70. Thus, in the case that the concentration of a nitrite ester in the first gas and the third gas becomes excessively high, the concentration of a nitrite ester in the first gas and the third gas can be decreased through decreasing the amount of the noncondensable gas to feed to the third reactor 70.

The concentration of a nitrite ester in the first gas and the third gas can be adjusted through changing operation conditions for the third reactor 70. For example, the amount of a nitrite ester to be formed through the reactions represented by the formula (5) and the formula (6) can be adjusted through changing mixing conditions for the bottom liquid and the noncondensable gas in the third reactor 70. The mixing conditions can be changed, for example, through regulation of the stirring speed of the third reactor 70, the amount of the bottom liquid to circulate, or the reaction temperature in the third reactor 70.

The position for the fourth gas flowing through the passage 71 and the noncondensable gas to join together is not particularly limited. However, the reaction in the second reactor 30 can be allowed to proceed more efficiently if the fourth gas from the third reactor 70 is allowed to join the noncondensable gas in the upstream side of oxygen gas, as illustrated in FIG. 1.

A part or all of the bottom liquid in the second reactor 30 may pass through a passage 92 linked to a passage 74, a cooler 90, and a passage 94 in the order presented to return to the second reactor 30. This enables easy control of the reaction temperature in the second reactor 30. The temperature in the second reactor 30 may be 10 to 60° C. It is preferable that the solution flowing through the passage 94 be returned to the intermediate part of the second reactor 30.

To the bottom of the third reactor 70, a passage 81 for extraction of the reaction solution is connected. The reaction solution obtained in the third reactor 70 and containing water, an alcohol, nitric acid, etc., flows through the passage 81 to be fed to a nitric acid-concentrating column 80. In the nitric acid-concentrating column 80, the reaction solution is heated. From a passage 84 connected to the top of the nitric acid-concentrating column 80, a part or all of water and an alcohol is obtained as a distillate. From a passage 82 connected to the bottom of the nitric acid-concentrating column 80, a concentrate of concentrated nitric acid is obtained. In the nitric acid-concentrating column 80, the concentration of an alcohol in the concentrate remaining in the bottom of the nitric acid-concentrating column 80 may be controlled to, for example, less than 4.0% by weight. This can prevent formation of a nitrate ester through a reaction of nitric acid and an alcohol in the bottom of the nitric acid-concentrating column 80. In view of safety, it is preferable to reduce the amount of a nitrate accumulated in the device.

The pressure in the nitric acid-concentrating column 80 is not particularly limited, and may be lower than the atmospheric pressure. Concentration of the reaction solution at a pressure lower than the atmospheric pressure can further lower the concentration of an alcohol in the concentrate. The pressure in the nitric acid-concentrating column 80 may be, for example, 6 to 70 kPa or may be 10 to 50 kPa. The temperature of the bottom of the nitric acid-concentrating column 80 may be, for example, 30 to 90° C., or may be 40 to 85° C. Lowering the temperature of the bottom of the nitric acid-concentrating column 80 can suppress the formation of a nitrate ester.

The distillate is extracted from the passage 84 connected to the upper part of the nitric acid-concentrating column 80. An alcohol separated from the distillate extracted from the passage 84 through distillation can be reused. An alcohol to be reused is temporarily stored in an alcohol tank as necessary, and can be fed to the second reactor 30, for example, from the passage 16 connected to the upper part of the second reactor 30.

A part of the concentrate concentrated in the nitric acid-concentrating column 80 flows through the passage 82 and a passage 73 connected to the passage 82 to be fed to the third reactor 70. A part of the concentrate may be allowed to flow through a passage 85 to be discharged as an effluent. The nitric acid-concentrating column 80 may be packed with a packing material such as a regular-shaped packing material and an irregular-shaped packing material to increase the number of theoretical plates for distillation. The number of theoretical plates of the nitric acid-concentrating column 80 may be one or more, or may be five or more.

The production device 100 includes the nitric acid-concentrating column 80 to distill off components with low boiling point from the reaction solution from the third reactor 70 to concentrate a nitric acid component. This enables effective utilization of a nitric acid component and the amount of a nitric acid component to be treated as an effluent can be sufficiently reduced. Accordingly, the amount of nitric acid or nitric oxide to be used as a raw material can be sufficiently reduced.

The third gas discharged from the top of the second reactor 30 flows through the passage 11, which is connected to the top, toward the first reactor 10. The passage 11 includes a junction part 55 to join a passage 18 to feed carbon monoxide. At the junction part 55, the third gas and carbon monoxide are mixed together. In the passage 11 in the downstream side of the junction part 55, a first measurement unit 40 to measure the concentration of a nitrite ester in the first gas and a second measurement unit 42 to measure the concentration of nitric oxide are provided.

Concentration information on the concentration of a nitrite ester measured in the first measurement unit 40 is input to a control unit 50 from the first measurement unit 40. The control unit 50 operates to control the flow rate of the noncondensable gas to feed to the third reactor 70 on the basis of concentration information from the first measurement unit 40. The control unit 50 includes, for example, a CPU (Central Processing Unit), a ROM (Read Only Memory), a RAM (Random Access Memory), and an input/output interface. A function to set an output to the first flow rate-adjusting unit 72 in accordance with concentration information for a nitrite ester in the first gas may be stored in the control unit 50.

Figure 2:
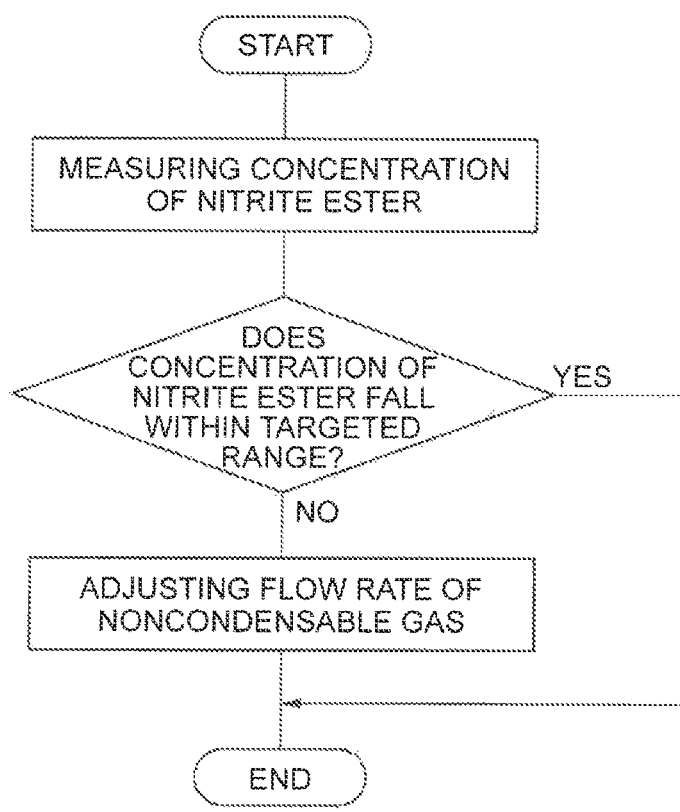
FIG. 2 is a flow chart illustrating a method for adjusting the flow rate of a noncondensable gas applied to the embodiment in FIG. 1.

FIG. 2 is a flow chart illustrating a method for adjusting the flow rate of the noncondensable gas applied to the production device 100. In the first measurement unit 40 in FIG. 1, the concentration of a nitrite ester in the first gas in the passage 11 is measured. The control unit 50 determines whether the concentration of a nitrite ester in the first gas falls within a targeted range on the basis of concentration information from the first measurement unit 40. The targeted range of the concentration of a nitrite ester may be 5 to 25% by volume based on the total of the first gas. If the concentration of a nitrite ester in the first gas measured in the first measurement unit 40 falls within the targeted range, the control unit 50 does not need to adjust the flow rate with the first flow rate-adjusting unit 72.

If the concentration of a nitrite ester in the first gas measured in the first measurement unit 40 is out of the targeted range, on the other hand, the control unit 50 changes a flow rate setting of the first flow rate-adjusting unit 72 to control the concentration of a nitrite ester within the targeted range. In the case that the first flow rate-adjusting unit 72 is a flow regulating valve, for example, the control unit 50 sets a targeted degree of opening for the flow regulating valve. For example, the control unit 50 sends a control signal for the targeted degree of opening to the first flow rate-adjusting unit 72. In this way, the control unit 50 may be configured to automatically control the first flow rate-adjusting unit 72.

In the case that the first flow rate-adjusting unit 72 is a flow regulating valve, the flow regulating valve includes an actuator including an electrical motor, and can change the degree of opening of the valve with the actuator. In the flow regulating valve, the actuator drives on the basis of a control signal from the control unit 50 to adjust the degree of opening of the valve. The flow regulating valve thus adjusts the flow rate of the noncondensable gas to the third reactor 70. In this way, the concentration of a nitrite ester in the first gas and the third gas can be controlled.

The method for adjusting the flow rate of the noncondensable gas to feed to the third reactor 70 is not limited to the above-described mode. For example, a flow rate-adjusting unit may be provided in the passage 13 in the downstream side of the branching point of the passage 13 and the passage 76 to adjust the amount of the noncondensable gas to be fed to the third reactor 70. Then, the flow rate-adjusting unit may have the same configuration as the first flow rate-adjusting unit 72.

Figure 3:
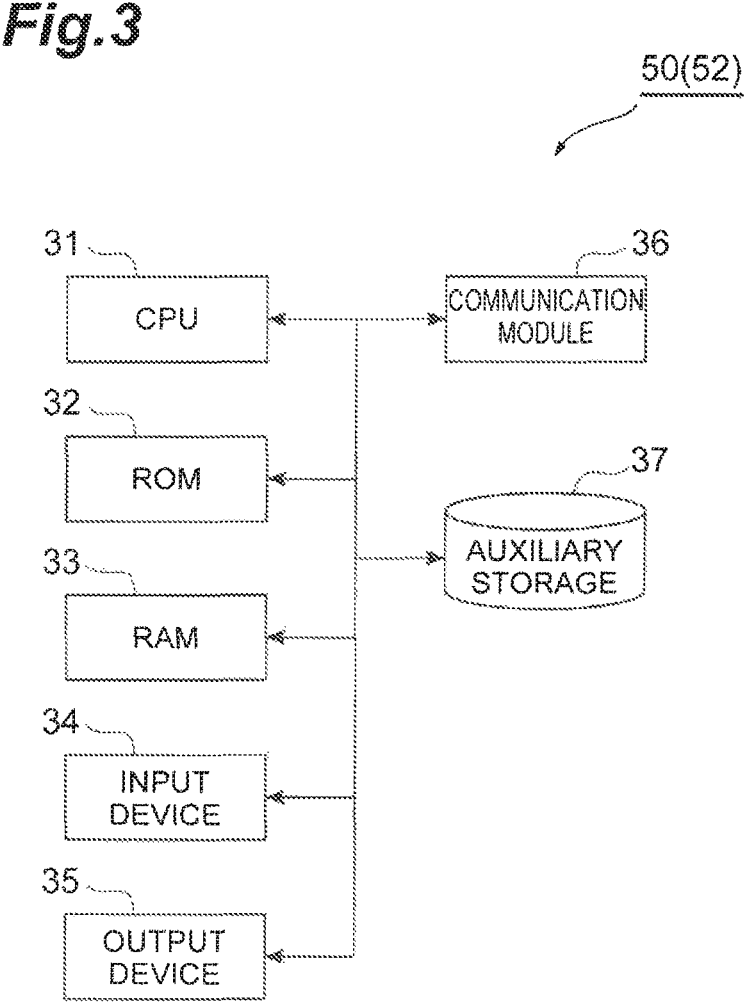
FIG. 3 is a hardware configuration diagram of a control unit.

FIG. 3 is a hardware configuration diagram of the control unit 50. As illustrated in FIG. 3, the control unit 50 can be physically configured as a common computer system including a CPU 31, a main memory such as a ROM 32 and a RAM 33, an input device 34 such as a keyboard and a mouse, an output device 35 such as a display, a communication module 36 such as a network card to send/receive data to/from, the first measurement unit 40 and the first flow rate-adjusting unit 72, and an auxiliary storage 37 such as a hard disk.

Signal processing and control functions of the control unit 50 are achieved by reading a predetermined computer software into a hardware such as the CPU 31, the ROM 32, and the RAM 33 so as to operate the input device 34, the output device 35, and the communication module 36 and reading and writing data from/in the ROM 32, the RAM 33, and the auxiliary storage 37 under control of the CPU 31. The ROM 32, the RAM 33, or the auxiliary storage 37 may store data and a function to calculate the concentration of a nitrite ester on the basis of an electrical signal input from the first measurement unit 40.

Common online analyzers using gas chromatography, mass spectrometry, infrared spectroscopy, chemiluminescence method with ozone, absorptiometry with a Zalzmann reagent, or the like may be used for the first measurement unit 40, and two or more of them may be combined. Among the analyzers, use of a non-dispersive infrared analyzer (NDIR) enables quick measurement of the concentration of a nitrite ester at a high precision.

Figure 4:
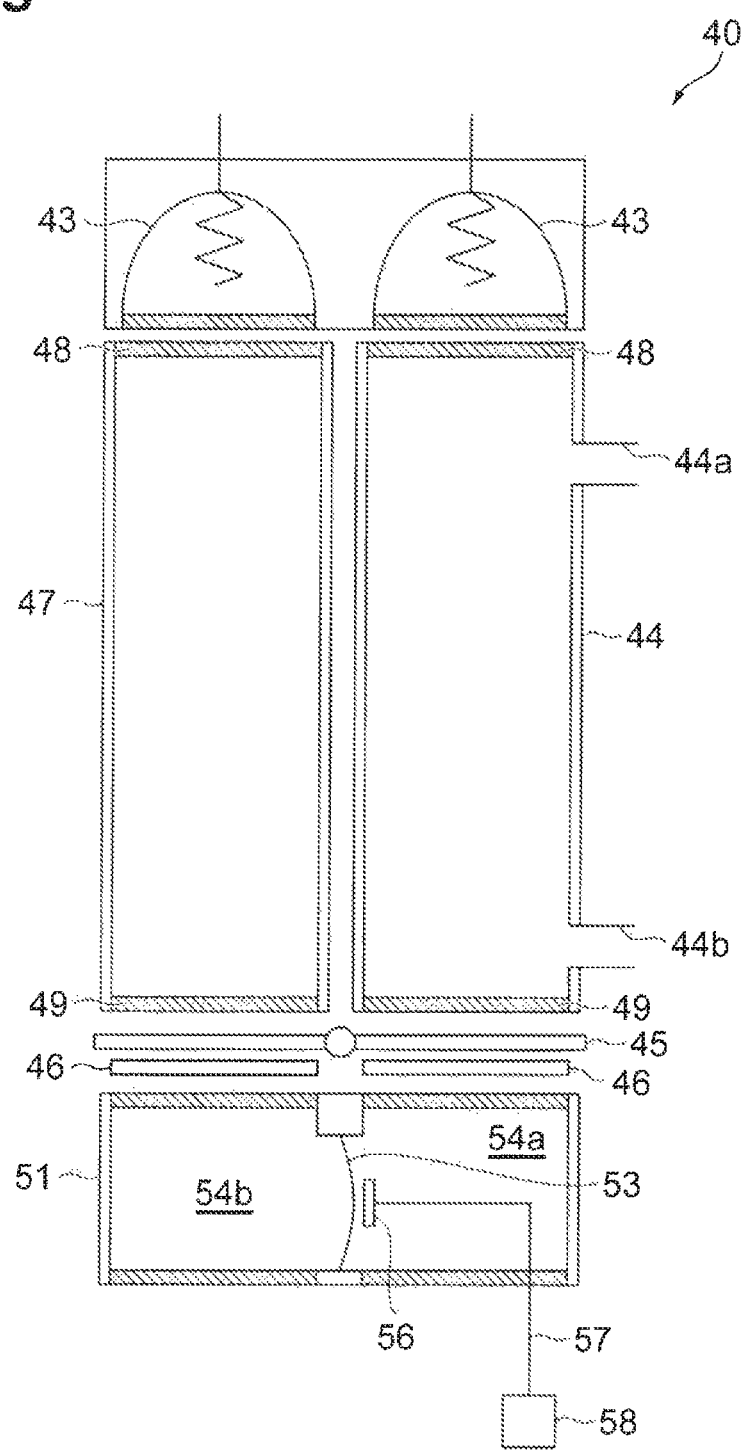
FIG. 4 illustrates an example of a non-dispersive infrared analyzer used in one embodiment.

FIG. 4 illustrates an example of a non-dispersive infrared analyzer used in the present embodiment. A non-dispersive infrared analyzer 40 includes: a pair of light sources 43, 43 to irradiate with an infrared ray; a measurement cell 44 to allow the first gas, as a subject to be measured, to flow therethrough; and a comparison cell 47 disposed in parallel with the measurement cell 44 and encapsulating an inert gas such as argon gas. At one end of each of the measurement cell 44 and the comparison cell 47, a transmission window 48 to allow an infrared ray from a light source 43 to transmit therethrough is provided. The measurement cell 44 and the comparison cell 47 are disposed in such a way that the transmission windows 48 of them are positioned opposite to the light sources 43, 43.

At another end of each of the measurement cell 44 and the comparison cell 47, a transmission window 49 to allow an infrared ray after passing through the measurement cell 44 or the comparison cell 47 to transmit therethrough is provided. An infrared ray after passing through each of the measurement cell 44 and the comparison cell 47 passes through the transmission window 49 and enters a detector 51 disposed opposite to the transmission window 49. Between the transmission window 49 and the detector 51, a light chopper 45 and an optical filter 46 are provided. The light chopper 45 allows an infrared ray after passing through each of the measurement cell 44 and the comparison cell 47 to intermittently enter the detector 51. The optical filter 46 allows an infrared ray within a predetermined wavenumber range to enter the detector 51.

The optical filter 46 absorbs an infrared ray within a specific wavenumber range. The optical filter 46 is selected so that an infrared ray with wavenumbers at which the infrared absorption band of a nitrite ester is detected enters the detector 51. In the case that a gas different from a nitrite ester (gas for detection) is encapsulated in the detector 51, the optical filter 46 is selected so that an infrared ray with wavenumbers including at least a part of wavenumbers in the infrared absorption band of a nitrite ester and at least a part of wavenumbers in the infrared absorption band of a gas for detection enters the detector 51. Accordingly, both a nitrite ester and a gas for detection have an infrared absorption band in the wavenumber range of an infrared ray entering the detector 51. Here, an infrared absorption band refers to a wavenumber range an infrared ray of which is absorbed.

The detector 51 is a capacitor microphone detector. The inner space of the detector 51 is separated by a thin membrane 53 provided near the center portion. As a result, a first chamber 54a and a second chamber 54b are formed in the detector 51. The light source 43 in one side, the measurement cell 44, and the first chamber 54a are disposed in series in the order presented. In parallel with this, the light source 43 in another side, the comparison cell 47, and the second chamber 54b are disposed in series in the order presented.

For the thin membrane 53, an insulating polymer film of a polyimide or the like on which an electroconductive film of a metal is formed through sputtering can be used. Into the first chamber 54a, an infrared ray after passing through the measurement cell 44 enters. Into the second chamber 54b, an infrared ray after passing through the comparison cell 47 enters. The detector 51 is configured to detect a nitrite ester on the basis of temperature difference between the first chamber 54a and the second chamber 54b.

An identical gas is encapsulated in the first chamber 54a and the second chamber 54b. For a gas to be encapsulated (gas for detection), a nitrite ester, as a subject to be measured, may be encapsulated. However, it is preferable to encapsulate a gas for detection consisting of a component which has an absorption peak in the wavenumber region including the absorption peaks of a nitrite ester, and is safer than nitrite esters and is not contained in the first gas (third gas), in view of further enhancement of safety. For such a gas for detection, ammonia can be used.

In the case that ammonia is used, the wavenumber range of an infrared ray entering the detector 51 may be controlled to, for example, 940 to 1080 cm$^{-1}$ with the optical filter 46. In the wavenumber range, a nitrite ester has absorption peaks due to N—O stretching vibration, etc. On the other hand, ammonia has absorption peaks due to $NH_2$ deformation vibration. In this way, a nitrite ester and ammonia each have absorption peaks in the above wavenumber range and other components (CO, NO) contained in the first gas each have few absorption peaks in the wavenumber range. Accordingly, the concentration of a nitrite ester can be measured at a high precision.

Figure 5:
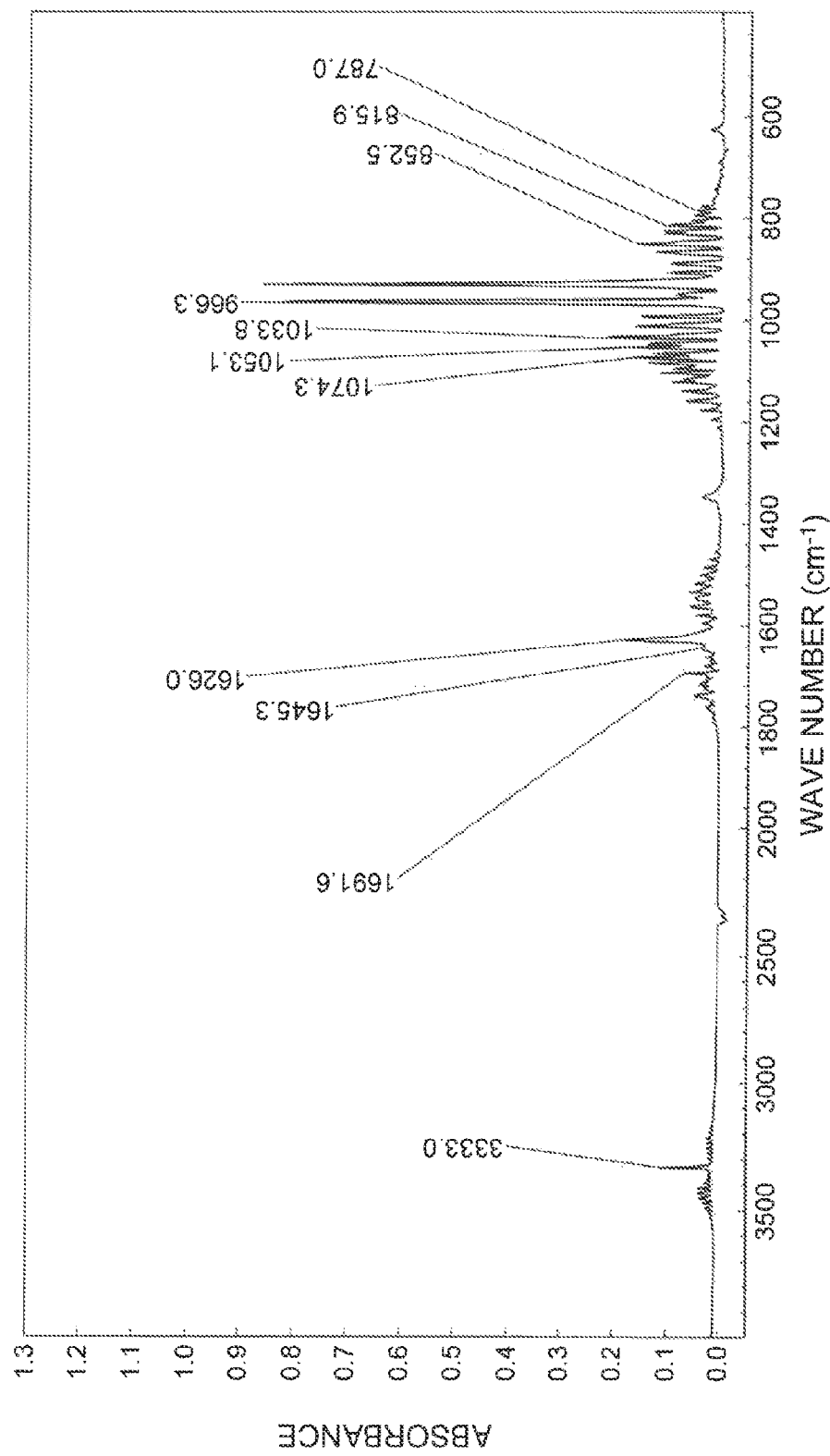
FIG. 5 is an absorption spectrum of ammonia.
Figure 6:
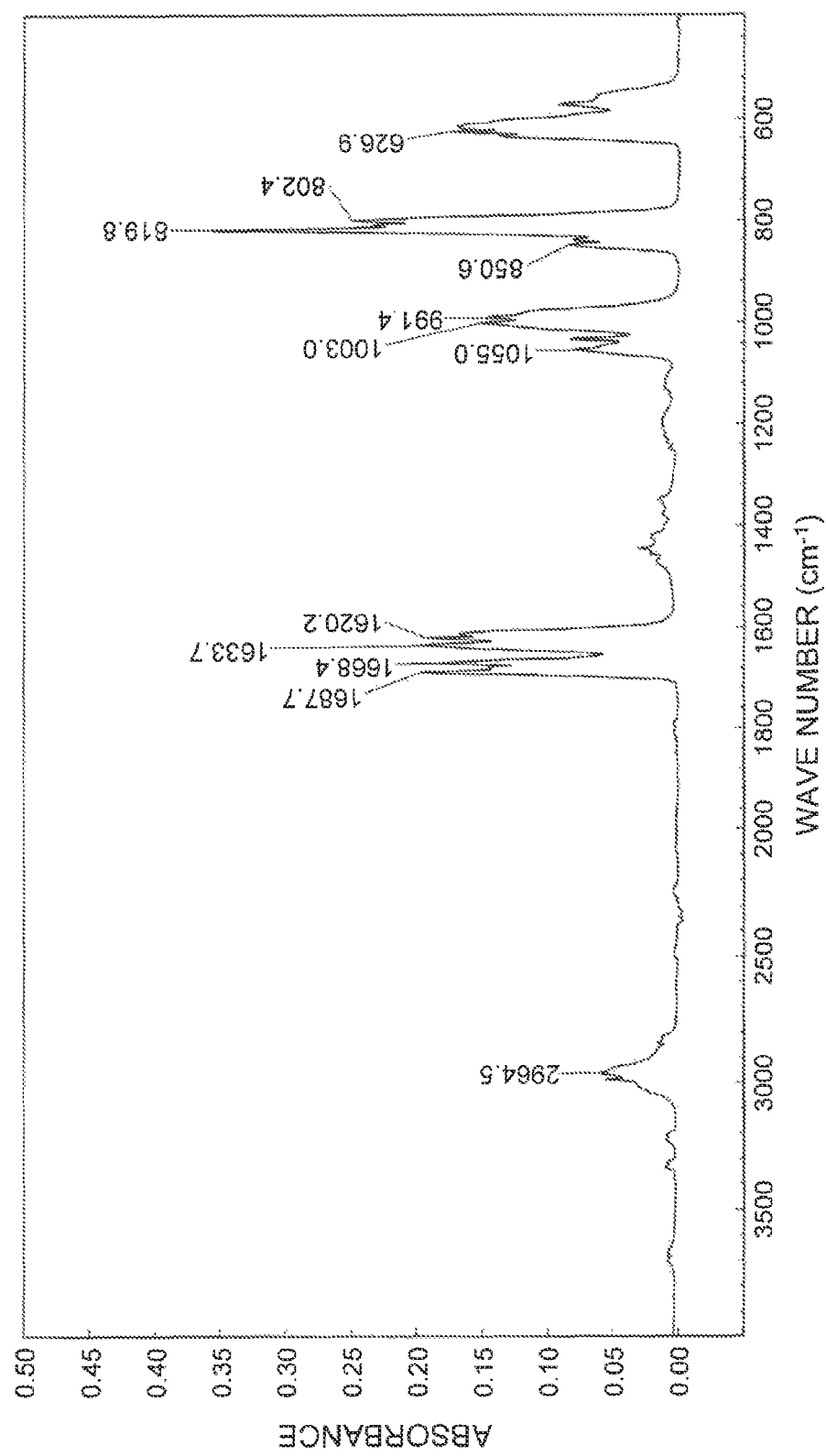
FIG. 6 is an absorption spectrum of a nitrite ester.

FIG. 5 is an infrared absorption spectrum of ammonia. FIG. 6 is an absorption spectrum of a nitrite ester. As can be seen from comparison of FIGS. 5 and 6, ammonia and a nitrite ester each have absorption peaks within a wavenumber range of 940 to 1080 cm$^{-1}$ and also within wavenumber ranges of 780 to 860 cm$^{-1}$ and 1650 to 1700 cm$^{-1}$. Thus, in the case that ammonia is used, the wavenumber range of an infrared ray entering the detector 51 may be 780 to 860 cm$^{-1}$ or 1650 to 1700 cm$^{-1}$. In addition, other components (CO, NO) contained in the first gas each have very few absorption peaks in the above wavenumber range. Accordingly, the concentration of a nitrite ester can be measured at a high precision. Here, the wavenumber range of 940 to 1080 cm$^{-1}$ roughly corresponds to a wavelength range of 926 to 1064 nm. The wavenumber range of 780 to 860 cm$^{-1}$ roughly corresponds to a wavelength range of 1163 to 1282 nm. The wavenumber range of 1650 to 1700 cm$^{-1}$ roughly corresponds to a wavelength range of 588 to 606 nm.

In the first chamber 54a, a fixed electrode 56 is disposed opposite to the thin membrane 53 as an electroconductive membrane, as illustrated in FIG. 4. To the fixed electrode 56, a lead 57 is connected. The lead 57 is connected to a signal processing unit 58. The signal processing unit 58 is, for example, a signal processing circuit. When a difference is made between the temperature of ammonia in the first chamber 54a and the temperature of ammonia in the second chamber 54b, the distance between the fixed electrode 56 and the thin membrane 53 changes. As a result, an electrical signal is output to the signal processing unit 58. By processing this electrical signal with the signal processing unit 58, the concentration of a nitrite ester can be measured. Calculation of the concentration of a nitrite ester may be performed in the control unit 50 on the basis of an electrical signal from the signal processing unit 58.

The method for measuring the concentration of a nitrite ester with the non-dispersive infrared analyzer 40 will be described. The first gas, which contains a nitrite ester and does not contain ammonia, (or the third gas) is introduced into the measurement cell 44 from a gas inlet 44a provided in one end side of the measurement cell 44. The first gas moves in the measurement cell from the upper side to the lower side in FIG. 4, and is discharged from a gas outlet 44b provided in another end side of the measurement cell 44. In the measurement cell 44, a nitrite ester contained in the first gas absorbs an infrared ray of a predetermined wavenumber range (L1) among infrared rays which have entered the measurement cell 44 from the light source 43. Thereafter, the infrared ray passes through the light chopper 45 and the optical filter 46 to enter the first chamber 54a of the detector 51. Then, ammonia encapsulated in the first chamber 54a absorbs the infrared ray of the predetermined wavenumber and the temperature is elevated. The temperature elevation is defined as $\Delta T1$.

On the other hand, the inert gas contained in the comparison cell 47 has no absorption peaks in any of the wavenumber regions of the absorption peaks of a nitrite ester. Thus, infrared rays entering from the light source 43 do not lose the infrared ray of the wavenumber range L1 through absorption, and the infrared rays including the infrared ray of the wavenumber range L1 enter the second chamber 54b of the detector 51. Then, ammonia encapsulated in the second chamber 54b absorbs the infrared rays including the infrared ray of the wavenumber range (L1) and the temperature is elevated. The temperature elevation is defined as $\Delta T2$. Infrared rays with the infrared ray of the wavenumber range L1 not being absorbed in passing through the comparison cell 47 enter the second chamber 54b. Accordingly, the temperature elevation of ammonia encapsulated in the second chamber 54b, $\Delta T2$, is higher than the temperature elevation of ammonia encapsulated in the first chamber 54a, $\Delta T1$. That is, the relation of $\Delta T1 < \Delta T2$ is satisfied.

This temperature difference ($\Delta T2 - \Delta T1$) changes the distance between the fixed electrode 56 and the thin membrane 53, and an electrical signal is transmitted. This signal is input into the signal processing unit 58 via the lead 57. The signal processing unit 58 processes the electrical signal to output the concentration of ammonia. The component to be measured (nitrite ester) is different from the component encapsulated in the detector 51 (ammonia). Accordingly, a measurement detected in the detector 51 may be corrected to determine the concentration of a nitrite ester more accurately. For example, the ratio of an integrated value around absorption peaks at the wavenumber range L1 between ammonia and a nitrite ester at an identical concentration (correction coefficient=integrated value around adsorption peaks of ammonia/integrated value around adsorption peaks of nitrite ester) is determined in advance. With use of this correction coefficient and a measurement detected in the detector 51, the concentration of a nitrite ester can be determined more accurately. Such correction may be performed in the signal processing unit 58 with a calculation program or the like, or may be performed in the control unit 50 or with another computer or the like.

Use of a non-dispersive infrared analyzer with a detector encapsulating ammonia for the first measurement unit 40 enables quick measurement of the concentration of a nitrite ester at a high precision, concomitantly with sufficient enhancement of the safety. The non-dispersive infrared analyzer is not limited to the mode illustrated in FIG. 3. For example, the detector may be a flow sensor detector to measure concentration by detecting movement of a gas (ammonia) which occurs in accordance with the change of the amount of an infrared ray. Alternatively, a compensating detector may be provided separately from the detector 51 between the measurement cell 44 and the comparison cell 47 and the detector 51, or in the side opposite to the measurement cell 44 and the comparison cell 47 in the detector 51.

For such a compensating detector, a compensating detector encapsulating a gas having very few absorption peaks in the infrared absorption bands of a nitrite ester can be used. By using a compensating detector and, for example, performing zero-drift correction, the concentration of a nitrite ester can be measured at a sufficiently high precision for a long period.

Figure 7:
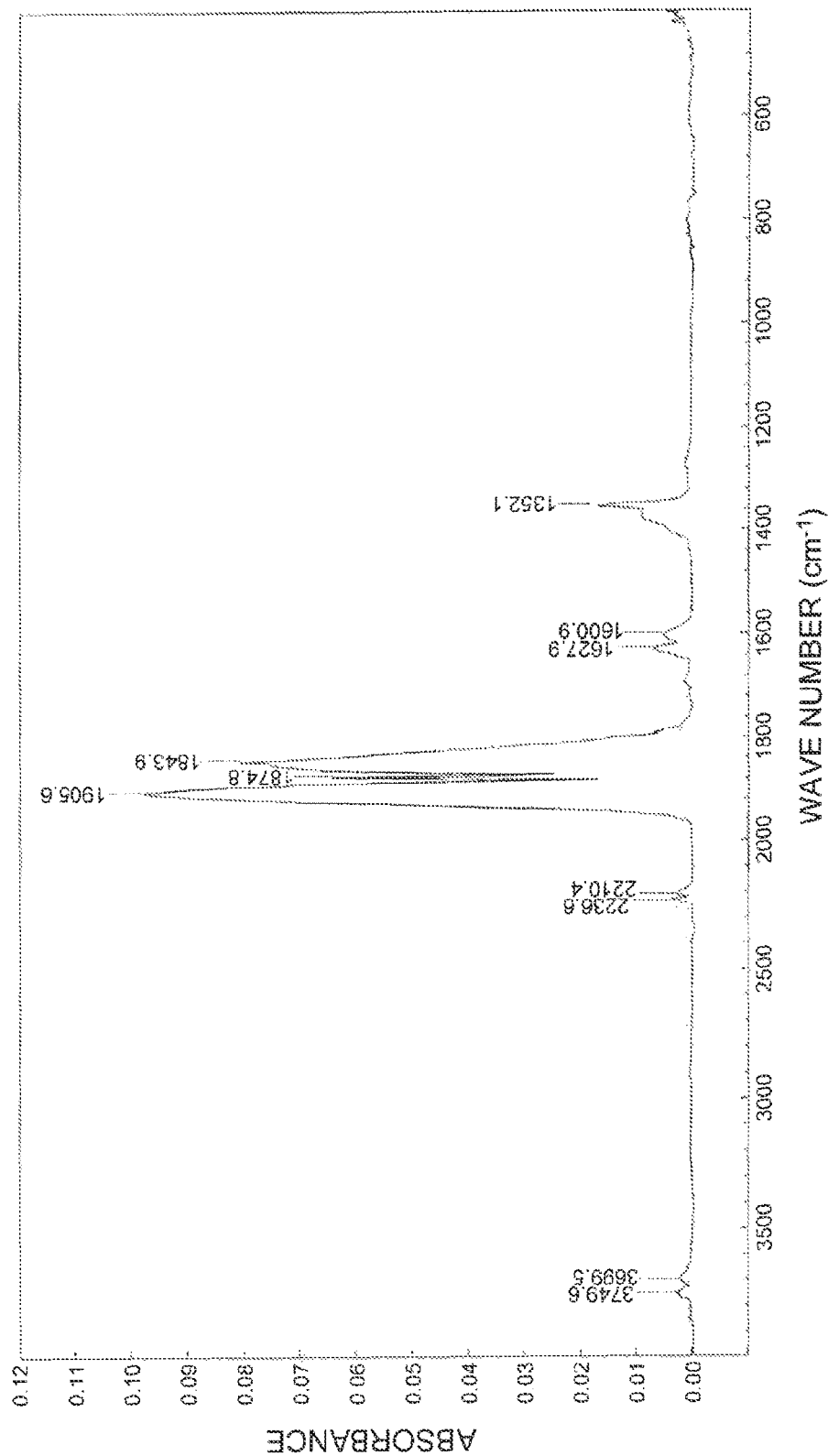
FIG. 7 is an absorption spectrum of nitric oxide.
Figure 8:
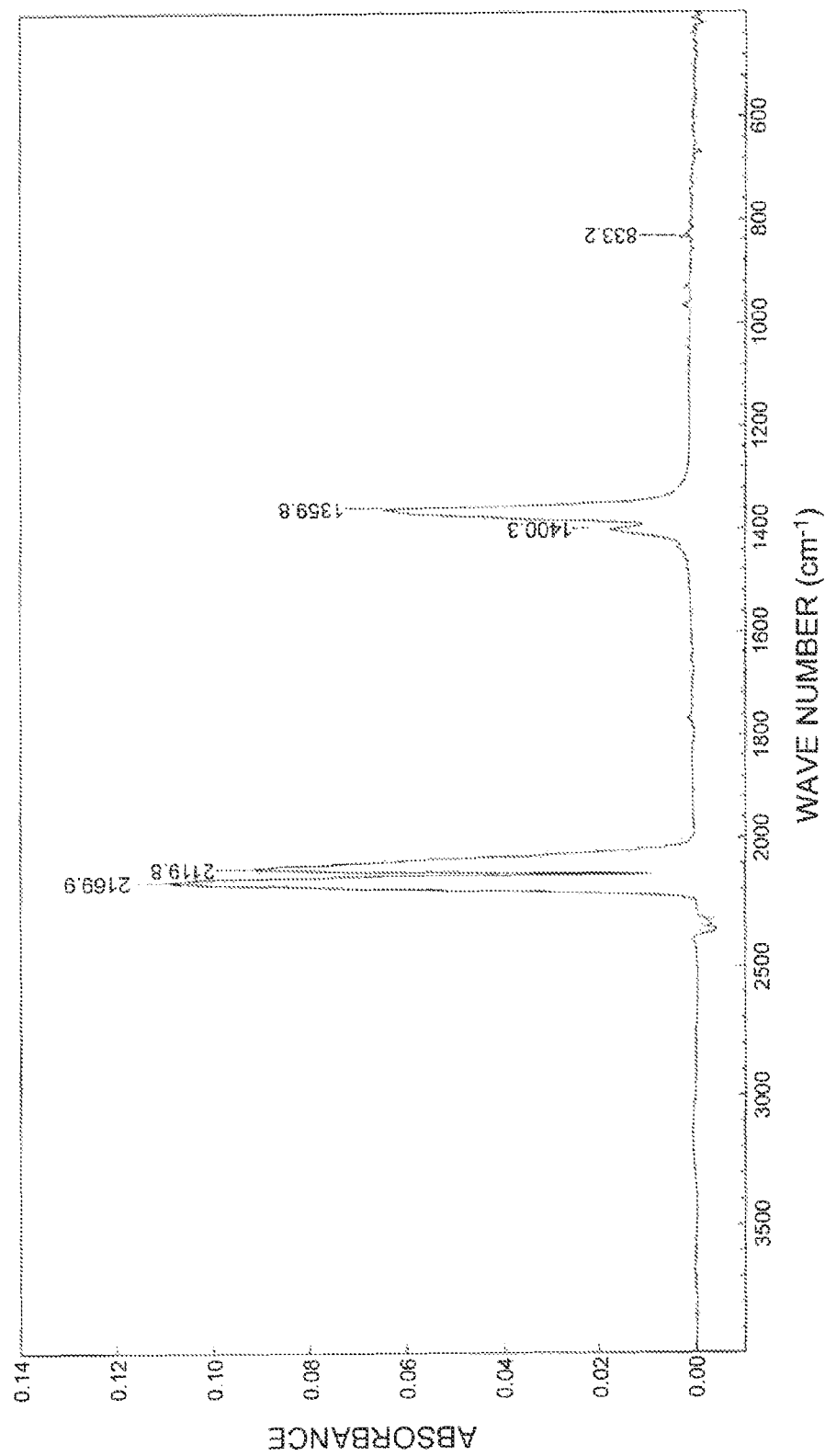
FIG. 8 is an absorption spectrum of carbon monoxide.

FIG. 7 is an infrared absorption spectrum of nitric oxide. FIG. 8 is an infrared absorption spectrum of carbon monoxide. Nitric oxide and carbon monoxide each have very few absorption peaks, for example, around 780 to 860 $cm^{-1}$, 940 to 1080 $cm^{-1}$, and 1650 to 1700 $cm^{-1}$ among the absorption peaks of a nitrite ester. Accordingly, even though the first gas contains nitric oxide and carbon monoxide, the concentration of methyl nitrite in the first gas can be measured at a high precision through appropriate selection of the wavenumber range of an infrared ray for measurement.

The production device 100 may further include the same measurement unit as the first measurement unit 40 to measure the concentration of nitric oxide, carbon monoxide, etc., in the first gas or the third gas. For example, a second measurement unit 42 to detect the concentration of nitric oxide is provided in the downstream side of the junction part 55 in FIG. 1. In accordance with the concentration of nitric oxide measured in the second measurement unit 42, information on the concentration of nitric oxide is input to a control unit 52 from the second measurement unit 42. Nitric oxide and carbon monoxide exhibit the infrared absorption spectrum as shown in FIG. 7 and FIG. 8, respectively. Accordingly, the concentration of nitric oxide and carbon monoxide may be determined by using infrared spectroscopy. However, the determination method is not limited to infrared spectroscopy.

The control unit 52 operates to control the amount of oxygen gas to mix with the noncondensable gas on the basis of information on the concentration of nitric oxide from the second measurement unit 42, and includes, for example, a CPU (Central Processing Unit), a ROM (Read Only Memory), a RAM (Random Access Memory), and an input/output interface. A function to adjust the fourth flow rate-adjusting unit 21 on the basis of concentration information for nitric oxide in the first gas may be stored in the control unit 52.

Figure 9:
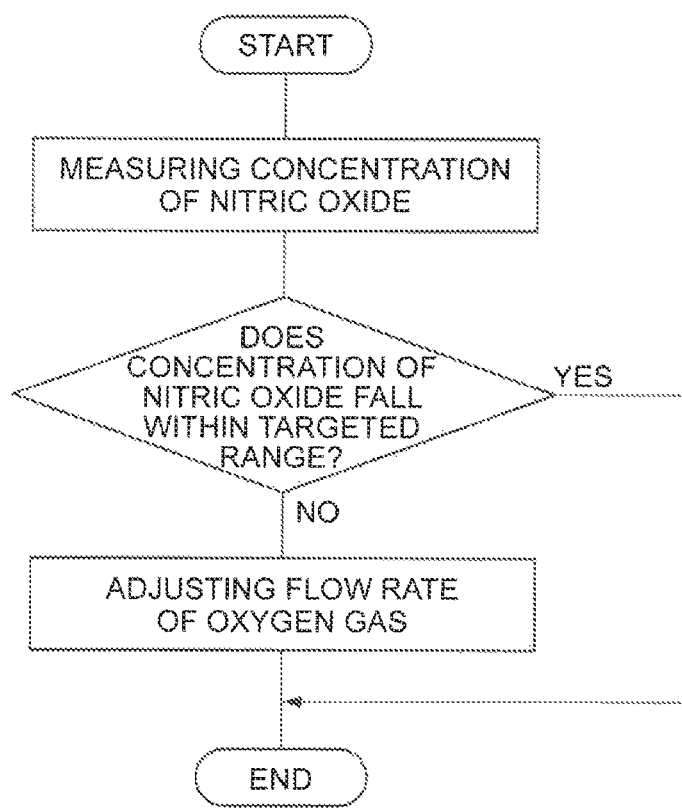
FIG. 9 is a flow chart illustrating a method for adjusting the flow rate of oxygen gas applied to one embodiment.

FIG. 9 is a flow chart illustrating a method for adjusting the flow rate of oxygen gas applied to the production device 100. In the second measurement unit 42 in FIG. 1, the concentration of nitric oxide in the first gas in the passage 11 is measured. The control unit 52 determines whether the concentration of nitric oxide in the first gas falls within a targeted range on the basis of concentration information for nitric oxide from the second measurement unit 42. The targeted range of the concentration of nitric oxide may be, for example, 5 to 50% by volume, or may be 15 to 40% by volume based on the total of nitric oxide and a nitrite ester. Alternatively, the targeted range of the concentration of nitric oxide may be, for example, 1 to 10% by volume, or may be 3 to 8% by volume based on the total of the first gas.

If the concentration of nitric oxide in the first gas measured in the second measurement unit 42 is out of the targeted range, on the other hand, the control unit 52 changes a flow rate setting of the fourth flow rate-adjusting unit 21 to control the concentration of nitric oxide within the targeted range. In the case that the fourth flow rate-adjusting unit 21 is a flow regulating valve, a targeted degree of opening (i.e., a targeted flow rate of oxygen gas) is set. For example, the control unit 52 sends a control signal for the targeted degree of opening to the fourth flow rate-adjusting unit 21. In this way, the control unit 52 may be configured to automatically control the fourth flow rate-adjusting unit 21.

As shown in FIG. 3, the control unit 52 can have the same configuration as the control unit 50. Thus, signal processing and control can be performed in the same manner as the control unit 50. The ROM 32, the RAM 33, or the auxiliary storage 37 may store data and a function to calculate the concentration of nitric oxide on the basis of an electrical signal input from the second measurement unit 42.

The reaction efficiency in the second reactor 30 and the concentration of oxygen in the first gas can be estimated and managed through measurement of the concentration of nitric oxide in the first gas in the second measurement unit 42. Specifically, if the concentration of nitric oxide in the first gas is high, oxygen in the second reactor 30 tends to be sufficiently consumed. Thus, an adverse effect on the catalytic activity in the first reactor 10 can be sufficiently lowered. If the concentration of nitric oxide in the first gas is low, on the other hand, the amount of unreacted oxygen in the second reactor 30 tends to increase. Thus, the catalytic activity in the first reactor 10 may be adversely affected.

Accordingly, lowering of the activity of the catalyst in the first reactor 10 can be sufficiently suppressed through maintaining the concentration of nitric oxide in the first gas within a predetermined range. In addition, a carbonate ester and/or an oxalic ester can be produced at a high production efficiency by setting an upper limit for nitric oxide in the first gas and adjusting the amount of oxygen gas to feed with the fourth flow rate-adjusting unit 21 so as not to exceed the upper limit. The targeted range of the concentration of a nitrite ester in the first gas may be, for example, 50 to 95% by volume, or may be 60 to 85% by volume based on the total of nitric oxide and a nitrite ester.

By measuring the concentration of both of a nitrite ester and nitric oxide in the first measurement unit 40 and the second measurement unit 42 and adjusting the flow rate with the first flow rate-adjusting unit 72 and the fourth flow rate-adjusting unit 21 on the basis of these measurement results, a carbonate ester and/or an oxalic ester can be produced more stably than in the case that the concentration of only a nitrite ester is measured and the flow rate is adjusted only with the first flow rate-adjusting unit 72.

Although, in the production device 100, the first measurement unit 40 and the second measurement unit 42 are provided in the downstream side of the junction part 55, that is, in a passage through which the first gas flows, the configuration is not limited thereto. In some other embodiments, for example, the first measurement unit 40 may detect the concentration of a nitrite ester and nitric oxide in the upstream side of the junction part 55, that is, in the third gas.

Figure 10:
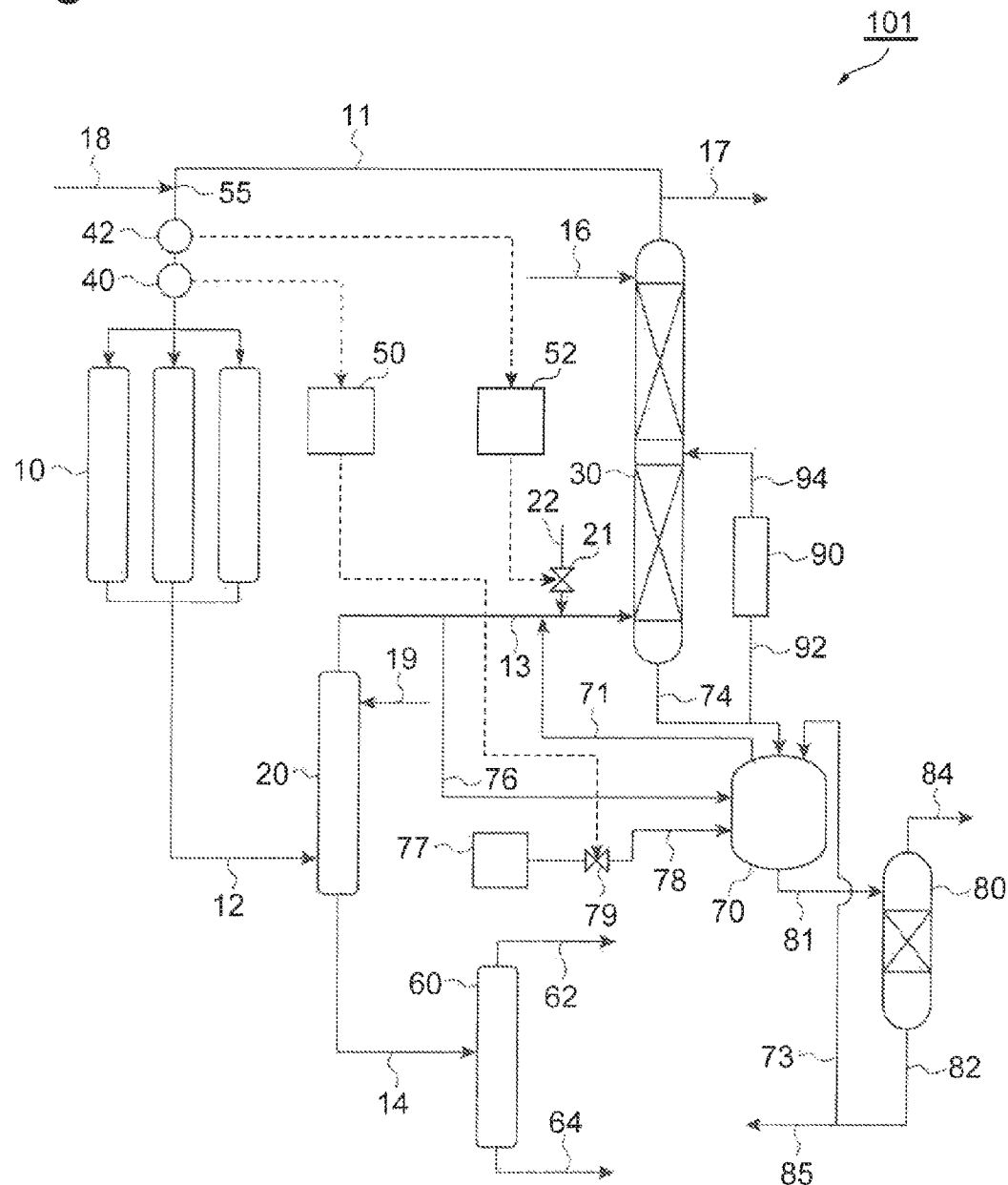
FIG. 10 schematically illustrates an ester production device according to another embodiment.

FIG. 10 schematically illustrates an ester production device according to another embodiment, where the ester is a carbonate ester and/or an oxalic ester. A production device 101 in FIG. 10 includes: a nitric acid tank 77 to stock nitric acid; a passage 78 to link the nitric acid tank 77 and a third reactor 70 together, and a second flow rate-adjusting unit 79 provided in the passage 78 to adjust the amount of nitric acid to feed to the third reactor 70. In addition, the production device 101 includes a control unit 50 configured to determine whether adjustment with the second flow rate-adjusting unit 79 is needed on the basis of the concentration of a nitrite ester measured in the first measurement unit 40 and adjust the flow rate of nitric acid with the second flow rate-adjusting unit 79, as necessary.

That is, the production device 101 is different from the production device 100 in that the production device 101 includes the nitric acid tank 77, the passage 78, and the second flow rate-adjusting unit 79 in place of the first flow rate-adjusting unit 72, and that the control unit 50 is configured to control the second flow rate-adjusting unit 79. The control unit 50 performs flow rate control with the second flow rate-adjusting unit 79 in the same manner as the flow rate control with the first flow rate-adjusting unit 72 in the production device 100. The other components of the production device 101 have the same configuration as in the case of the production device 100.

Figure 11:
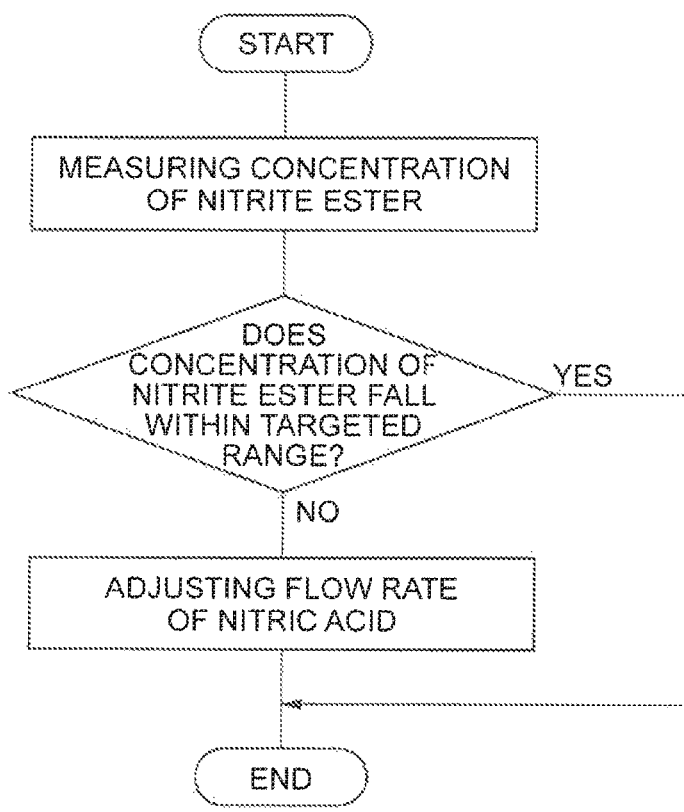
FIG. 11 is a flow chart illustrating a method for adjusting the flow rate of nitric acid applied to the embodiment in FIG. 10.

FIG. 11 is a flow chart illustrating a method for adjusting the flow rate of nitric acid applied to the production device 101. In the first measurement unit 40, the concentration of a nitrite ester in the first gas is measured. The control unit 50 determines whether the concentration of a nitrite ester measured in the first measurement unit 40 falls within a targeted range. If the concentration of a nitrite ester in the first gas measured in the first measurement unit 40 falls within a targeted range, the control unit 50 does not need to adjust the flow rate with the second flow rate-adjusting unit 79.

If the concentration of a nitrite ester in the first gas measured in the first measurement unit 40 is out of a targeted range, on the other hand, the control unit 50 changes a flow rate setting of the second flow rate-adjusting unit 79 to control the concentration of a nitrite ester within a targeted range. In the case that the second flow rate-adjusting unit 79 is a flow regulating valve, the flow regulating valve includes an actuator including an electrical motor, and can change the degree of opening of the valve with the actuator. In the flow regulating valve, the actuator drives on the basis of a control signal from the control unit 50 to adjust the degree of opening of the valve. The second flow rate-adjusting unit 79 thus adjusts the amount of nitric acid to feed to the third reactor 70.

In the case that the amount of nitric acid is insufficient in the third reactor 70 to thereby tend to decrease the concentration of a nitrite ester measured in the first measurement unit 40 or to thereby allow the concentration of a nitrite ester to reach the lower limit, the control unit 50 adjusts the second flow rate-adjusting unit 79 to increase the amount of nitric acid to feed to the third reactor 70. As a result, the reactions represented by the above formula (5) and formula (6) are accelerated to increase the amount of a nitrite ester formed, and thus the concentration of a nitrite ester in the first gas and the third gas can be increased.

In the case that the concentration of a nitrite ester measured in the first measurement unit 40 tends to increase, or reaches the upper limit, on the other hand, the control unit 50 adjusts the second flow rate-adjusting unit 79 to decrease the amount of nitric acid to feed to the third reactor 70. As a result, the reactions represented by the above formula (5) and formula (6) are inhibited to decrease the amount of a nitrite ester formed, and thus the concentration of a nitrite ester in the first gas and the third gas can be decreased. In this way, the concentration of a nitrite ester in the first gas and the third gas can be controlled.

Figure 12:
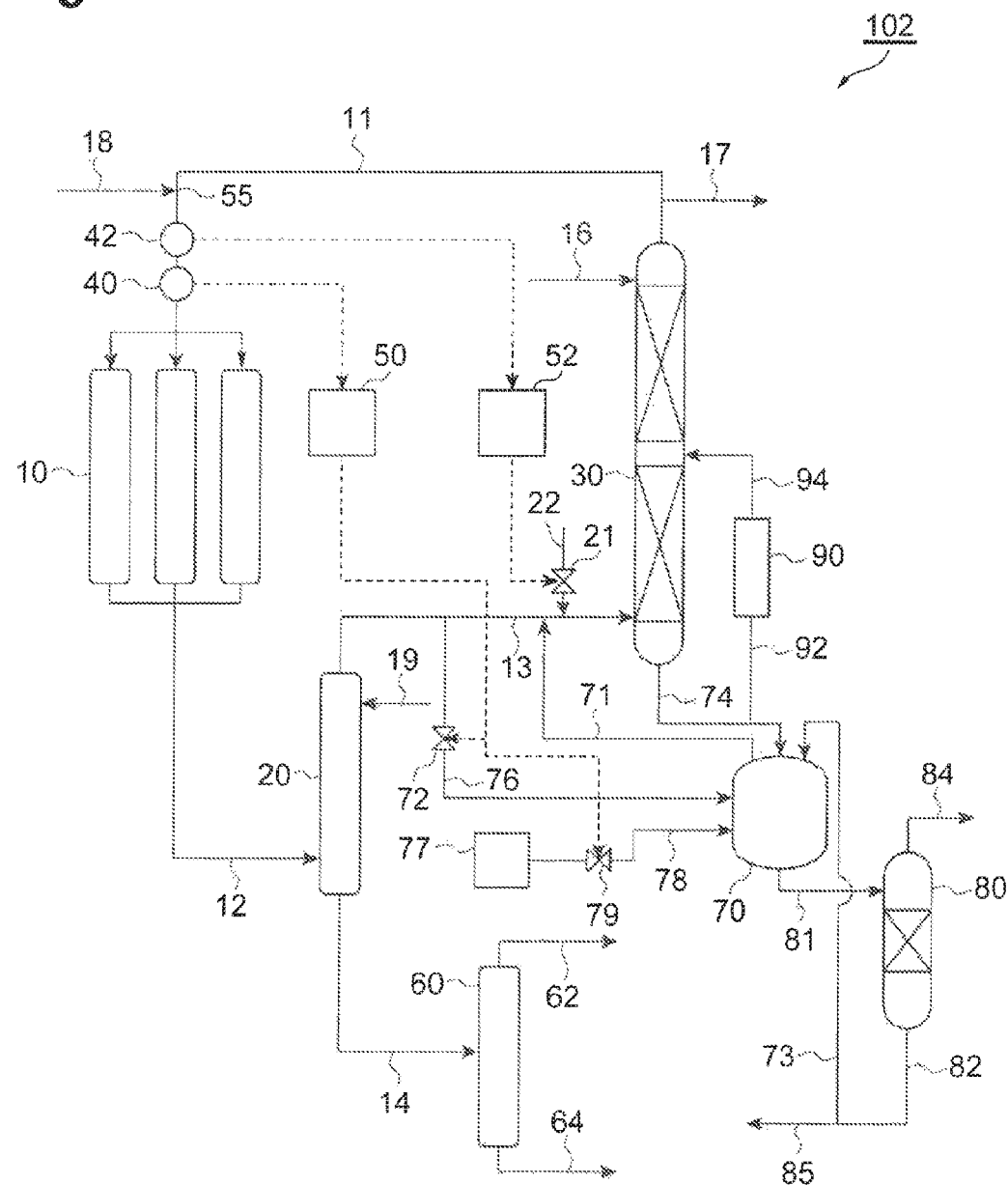
FIG. 12 schematically illustrates an ester production device according to still another embodiment.

FIG. 12 schematically illustrates an ester production device according to still another embodiment, where the ester is a carbonate ester and/or an oxalic ester. As is the case with the production device 101 in FIG. 10, a production device 102 in FIG. 12 includes: a nitric acid tank 77 to stock nitric acid; a passage 78 to link the nitric acid tank 77 and a third reactor 70 together; and a second flow rate-adjusting unit 79 provided in the passage 78 to adjust the amount of nitric acid to feed to the third reactor 70. In addition, the production device 102 includes, as is the case with the production device 100 in FIG. 1, a first flow rate-adjusting unit 72 to adjust the amount of the noncondensable gas to feed to the third reactor 70.

The production device 102 includes a control unit 50 configured to determine whether adjustment with the first flow rate-adjusting unit 72 and/or the second flow rate-adjusting unit 79 is needed on the basis of a measurement result of the first measurement unit 40 and adjust the amount of the noncondensable gas and/or nitric acid to feed with the first flow rate-adjusting unit 72 and/or the second flow rate-adjusting unit 79, as necessary. That is, the production device 102 is different from the production device 101 in that the production device 102 includes the first flow rate-adjusting unit 72, and that the control unit 50 is configured to control not only the second flow rate-adjusting unit 79 but also the first flow rate-adjusting unit 72. The other components of the production device 102 have the same configuration as in the case of the production devices 100, 101.

The production device 102 includes: a first measurement unit 40 to measure the concentration of a nitrite ester in the first gas; a first flow rate-adjusting unit 72 to adjust the amount of the noncondensable gas to feed to the third reactor 70; a second flow rate-adjusting unit 79 to adjust the amount of nitric acid to feed to the third reactor 70; and a control unit 50 configured to determine whether adjustment with the first flow rate-adjusting unit 72 and/or the second flow rate-adjusting unit 79 is needed on the basis of the concentration of a nitrite ester measured in the first measurement unit 40 and adjust the flow rate of the noncondensable gas with the first flow rate-adjusting unit 72 and/or adjust the flow rate of nitric acid with the second flow rate-adjusting unit 79. The control unit 50 performs flow rate control with the first flow rate-adjusting unit 72 and the second flow rate-adjusting unit 79 in the same manner as the flow rate control with the first flow rate-adjusting unit 72 in the production device 100 and the flow rate control with the second flow rate-adjusting unit 79 in the production device 101.

Figure 13:
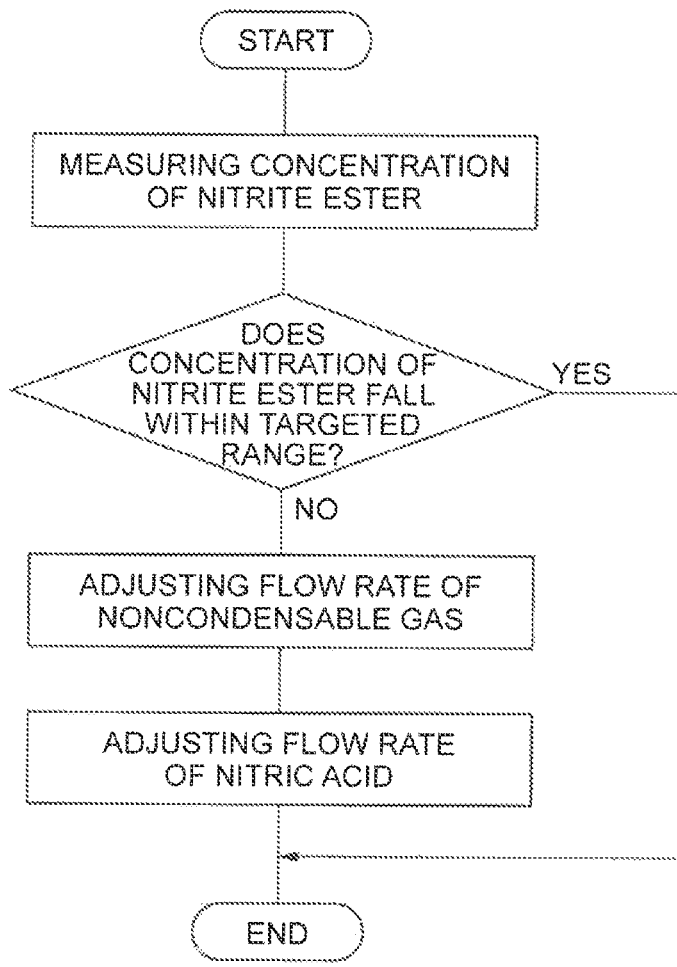
FIG. 13 is a flow chart illustrating a method for adjusting the flow rate of a noncondensable gas and nitric acid applied to the embodiment in FIG. 12.

FIG. 13 is a flow chart illustrating a method for adjusting the flow rate of nitric acid applied to the production device 102. In the first measurement unit 40, the concentration of a nitrite ester in the first gas is measured. The control unit 50 determines whether the concentration of a nitrite ester in the first gas falls within a targeted range. If the concentration of a nitrite ester in the first gas measured in the first measurement unit 40 falls within a targeted range, flow rate adjustment with the first flow rate-adjusting unit 72 and the second flow rate-adjusting unit 79 is not required.

If the concentration of a nitrite ester in the first gas measured in the first measurement unit 40 is out of a targeted range, on the other hand, the control unit 50 changes a flow rate setting of the first flow rate-adjusting unit 72 and the second flow rate-adjusting unit 79 to control the concentration of a nitrite ester within a targeted range. Thus, the amount of the noncondensable gas and nitric acid to feed to the third reactor 70 is adjusted. Flow rate adjustment with the first flow rate-adjusting unit 72 and the second flow rate-adjusting unit 79 may be performed in the order of flow rate adjustment of the noncondensable gas with the first flow rate-adjusting unit 72 and flow rate adjustment of nitric acid with the second flow rate-adjusting unit 79, as illustrated in FIG. 13, or may be performed in the reverse order. Alternatively, flow rate adjustment of the noncondensable gas and nitric acid may be performed simultaneously, or the control unit 50 may select only one of them to perform flow rate adjustment. In this way, the concentration of a nitrite ester in the first gas and the third gas can be controlled.

Figure 14:
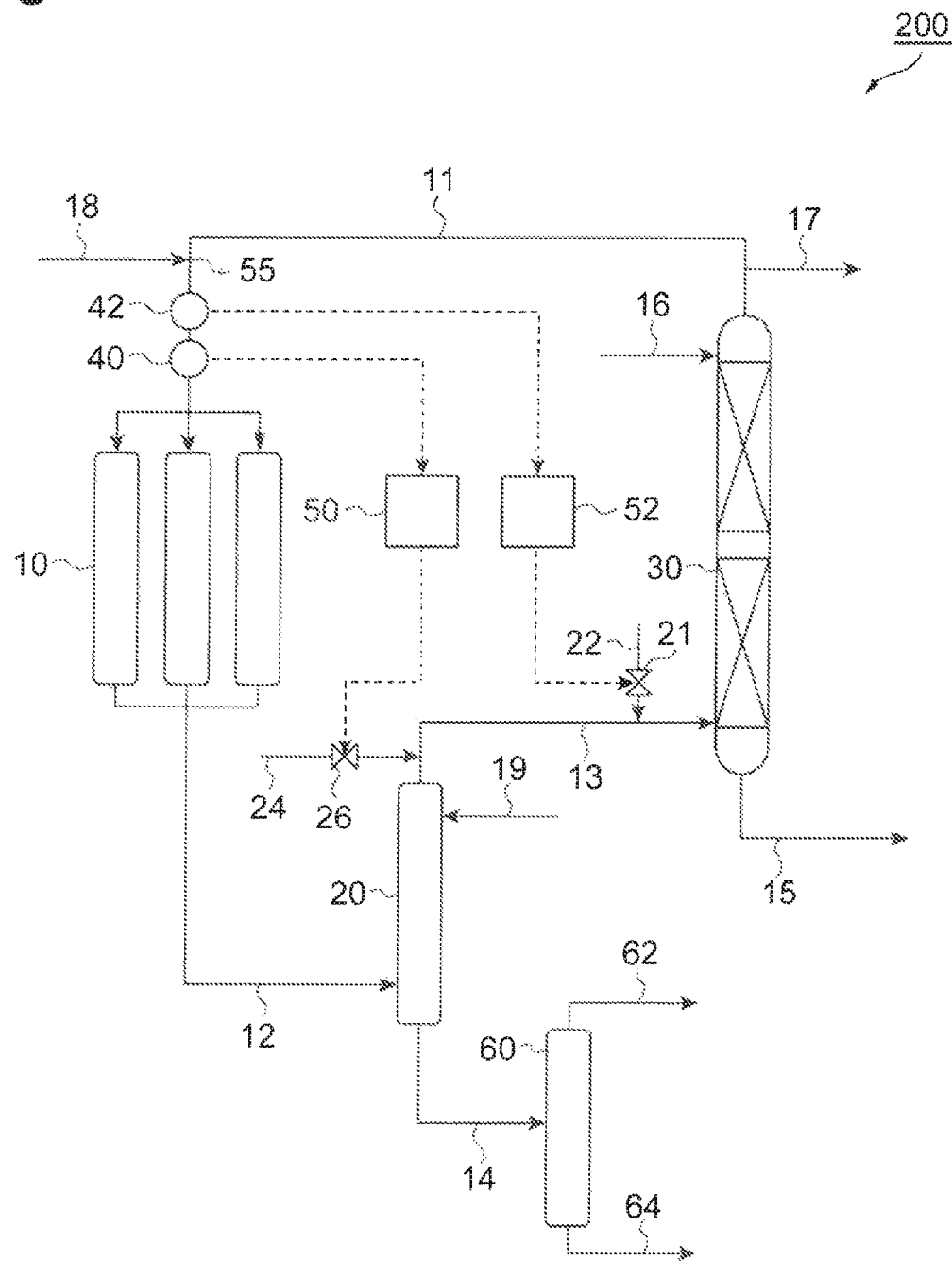
FIG. 14 schematically illustrates an ester production device according to still another embodiment.

FIG. 14 schematically illustrates an ester production device according to still another embodiment, where the ester is a carbonate ester and/or an oxalic ester. A production device 200 in FIG. 14 is different from the production device 100 in FIG. 1 in that the production device 200 does not include a third reactor and a nitric acid-concentrating column, and that the production device 200 includes a passage 24 to feed nitric oxide and a third flow rate-adjusting unit 26 to adjust the amount of nitric oxide to feed. Since the production device 200 does not include a third reactor, the bottom liquid in the second reactor 30 is sent to recovery equipment or disposal equipment, which is not illustrated, through a passage 15. The bottom liquid contains water, nitric acid, and an alcohol. These components may be treated for reuse with recovery equipment provided in the downstream side, as necessary.

In the case that the bottom liquid in the second reactor 30 is discharged to the outside of the production device 200 in this way, nitric oxide is fed. Feeding of nitric oxide can be performed with the passage 24 connected to the passage 13. In the passage 24, the third flow rate-adjusting unit 26 to adjust the amount of nitric oxide to feed is provided. The function and configuration of the first measurement unit 40 and the control unit 50 may be the same as in the case of the production device 100 according to the above embodiment. For example, the control unit 50 sets the amount of nitric oxide to feed on the basis of concentration information on the concentration of a nitrite ester from the first measurement unit 40. The third flow rate-adjusting unit 26 adjusts the amount of nitric oxide to feed on the basis of a control signal from the control unit 50. Examples of the third flow rate-adjusting unit 26 include a flow regulating valve. In the case of a flow regulating valve, the amount of nitric oxide to feed can be adjusted through changing the degree of opening of the valve.

Figure 15:
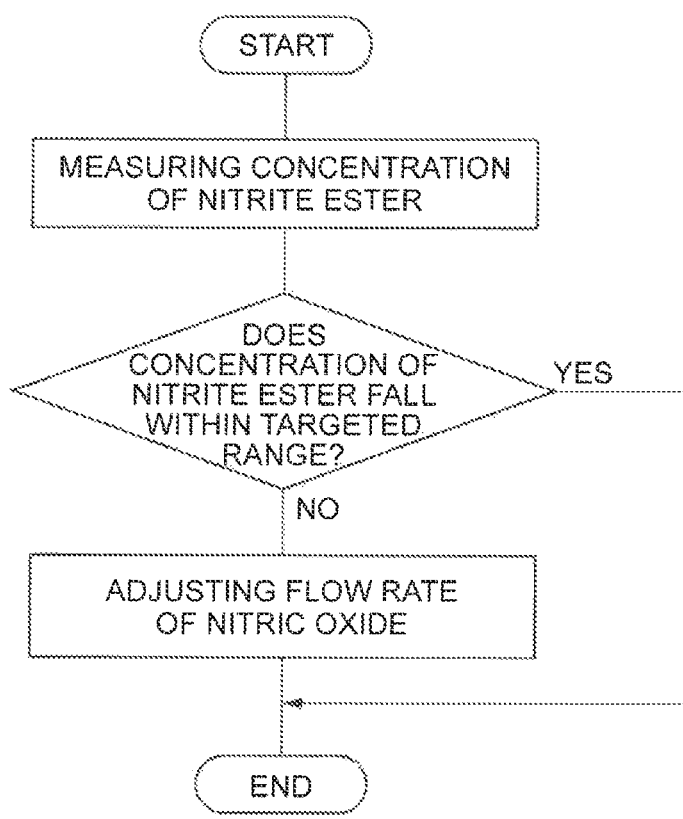
FIG. 15 is a flow chart illustrating a method for adjusting the flow rate of nitric oxide applied to the embodiment in FIG. 14.

FIG. 15 is a flow chart illustrating a method for adjusting the flow rate of nitric oxide applied to the production device 200. In the first measurement unit 40, the concentration of a nitrite ester in the first gas is measured. The control unit 50 determines whether the concentration of a nitrite ester in the first gas falls within a targeted range on the basis of concentration information from the first measurement unit 40. If the concentration of a nitrite ester in the first gas measured in the first measurement unit 40 falls within a targeted range, flow rate adjustment with the third flow rate-adjusting unit 26 is not required.

If the concentration of a nitrite ester in the first gas measured in the first measurement unit 40 is out of a targeted range, on the other hand, the control unit 50 changes a flow rate setting of the third flow rate-adjusting unit 26 to control the concentration of a nitrite ester within a targeted range. In this way, the third flow rate-adjusting unit 26 adjusts the amount of nitric oxide to feed to the passage 13.

Nitric oxide whose flow rate has been adjusted with the third flow rate-adjusting unit 26 is allowed to mix with the noncondensable gas flowing through the passage 13. If the amount of nitric oxide to feed is increased, chemical reactions represented by the following formula (7) and formula (8) proceed. As a result, the concentration of oxygen contained in the first gas and the third gas decreases and the amount of a nitrite ester increases. In the formula (8), R denotes an alkyl group.

$$2NO + \frac{1}{2}O_2 \rightarrow N_2O_3 \tag{7}$$

$$N_2O_3 + 2ROH \rightarrow 2RONO + H_2O \tag{8}$$

The concentration of oxygen and a nitrite ester in the first gas and the third gas can be adjusted by adjusting the amount of nitric oxide to feed with the third flow rate-adjusting unit 26. In the case that the concentration of a nitrite ester measured in the first measurement unit 40 tends to increase, or is going to exceed the upper limit, the third flow rate-adjusting unit 26 reduces the amount of nitric oxide to feed or stops feeding on the basis of a control signal from the control unit 50. Through such an operation, the concentration of a nitrite ester in the first gas can be decreased. Then, the amount of oxygen to feed may be reduced with the fourth flow rate-adjusting unit 21 in combination with the above operation. Thus, the concentration of a nitrite ester in the first gas and the third gas can be smoothly decreased.

If the concentration of a nitrite ester in the first gas and the third gas tends to decrease, or is going to fall below the lower limit, on the other hand, the amount of nitric oxide to feed is increased with the third flow rate-adjusting unit 26. Then, the amount of oxygen to feed may be increased with the fourth flow rate-adjusting unit 21 in combination with this. Thus, the concentration of a nitrite ester in the first gas and the third gas can be smoothly increased.

The production device 200, having such a configuration, provides high safety, and can suppress lowering of the reaction rate in the first reactor 10 sufficiently. Accordingly, at least one of a carbonate ester and an oxalic ester can be produced stably.

The other configurations of the production device 200 are the same as in the case of the production device 100. The position at which nitric oxide is fed is not limited to the passage 13, and for example, nitric oxide may be fed to the passage 12, or may be fed directly to the second reactor 30.

Figure 16:
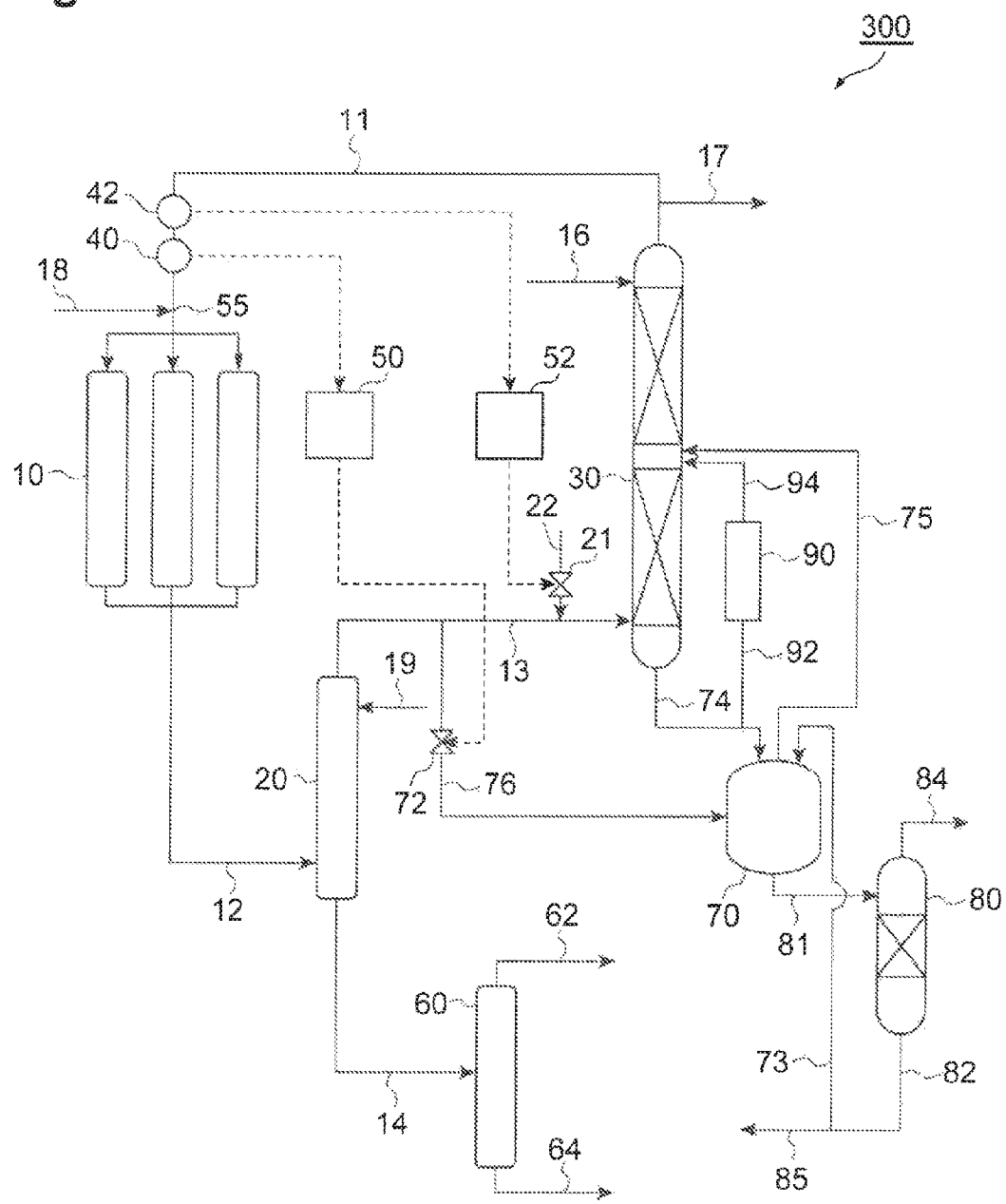
FIG. 16 schematically illustrates an ester production device according to still another embodiment.

FIG. 16 schematically illustrates an ester production device according to still another embodiment, where the ester is a carbonate ester and/or an oxalic ester. A production device 300 in FIG. 16 is different in that a first measurement unit 40 and a second measurement unit 42 are provided in the upstream side of a junction part 55, and that the fourth gas from a third reactor 70 is allowed to flow through a passage 75 to feed to the intermediate part of a second reactor 30. Configurations other than these points are the same as in the case of the production device 100.

By providing the first measurement unit 40 and the second measurement unit 42 in the upstream side of the junction part 55 as in FIG. 16, the concentration of a nitrite ester and the concentration of nitric oxide in the third gas can be measured. The control unit 50 may control the first flow rate-adjusting unit 72 so that the concentration of a nitrite ester in the third gas becomes, for example, 5 to 30% by volume. The control unit 52 may control the fourth flow rate-adjusting unit 21 so that the concentration of nitric oxide in the third gas falls within a predetermined range. By feeding the fourth gas from the third reactor 70 to the intermediate part of the second reactor 30 via the passage 75 as in FIG. 16, a nitrite ester can be formed more efficiently. The production device 300, having such a configuration, provides high safety, and can suppress lowering of the reaction rate in the first reactor 10 sufficiently. Accordingly, at least one of a carbonate ester and an oxalic ester can be produced stably.

The present invention is not limited to the above-described embodiments, and for example, the first measurement unit 40 and/or the second measurement unit 42 may be provided in both of the upstream side and the downstream side of the junction part 55. In this case, for example, the control units 50, 52 may be configured to control the first flow rate-adjusting unit 72, the second flow rate-adjusting unit 79, and the fourth flow rate-adjusting unit 21 on the basis of measurements for both of the first gas and the third gas. The control units 50, 52, which have different functions, may be integrally configured in terms of hardware.

It is not required to provide the second measurement unit 42 to measure the concentration of nitric oxide contained in the first gas and/or the third gas, the control unit 52, and the fourth flow rate-adjusting unit 21. The third reactor 70 and the nitric acid-concentrating column 80 may be included as the production devices 100, 101, 102, 300, or the passage 24 to feed nitric oxide and the third flow rate-adjusting unit 26 to adjust the amount thereof to feed may be included as the production device 200. In this case, the control unit 50 may be configured to select at least one of the third flow rate-adjusting unit 26, the first flow rate-adjusting unit 72, and the second flow rate-adjusting unit 79 to perform flow rate control, or to perform flow rate control for all of them simultaneously. In addition, the third reactor 70 is not limited to the above-described mode.

Figure 17:
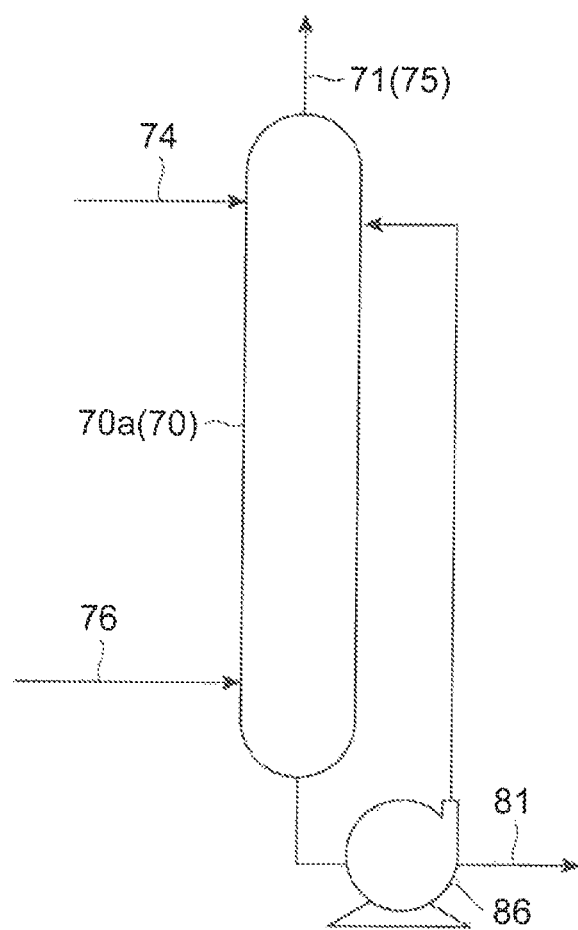
FIG. 17 schematically illustrates a modification of a third reactor in an ester production device according to one embodiment.

FIG. 17 illustrates a modification of the third reactor 70 in the production devices according to the above-described embodiments. The third reactor 70a in FIG. 17 is a bubbling tank. To the third reactor 70a, the bottom liquid in the second reactor 30 is fed from the passage 74, and the noncondensable gas is fed from the passage 76. In the third reactor 70a, the noncondensable gas is fed into the bottom liquid remaining in the bottom for bubbling. The bottom liquid which has remained for a predetermined period in the third reactor 70a is discharged from the bottom, and then fed to the nitric acid-concentrating column 80 through the passage 81.

A part of the bottom liquid discharged from the bottom of the third reactor 70a may be circulated with a pump 86 or the like. If the amount of the bottom liquid to circulate is increased, the reactions represented by the above formula (5) and formula (6) are accelerated to increase the amount of a nitrite ester formed. Thus, the concentration of a nitrite ester in the first gas and the third gas can be increased. The fourth gas discharged from the upper part of the third reactor 70a and containing a nitrite ester flows through the passage 71 or the passage 75, and then is fed to the second reactor 30.

Figure 18:
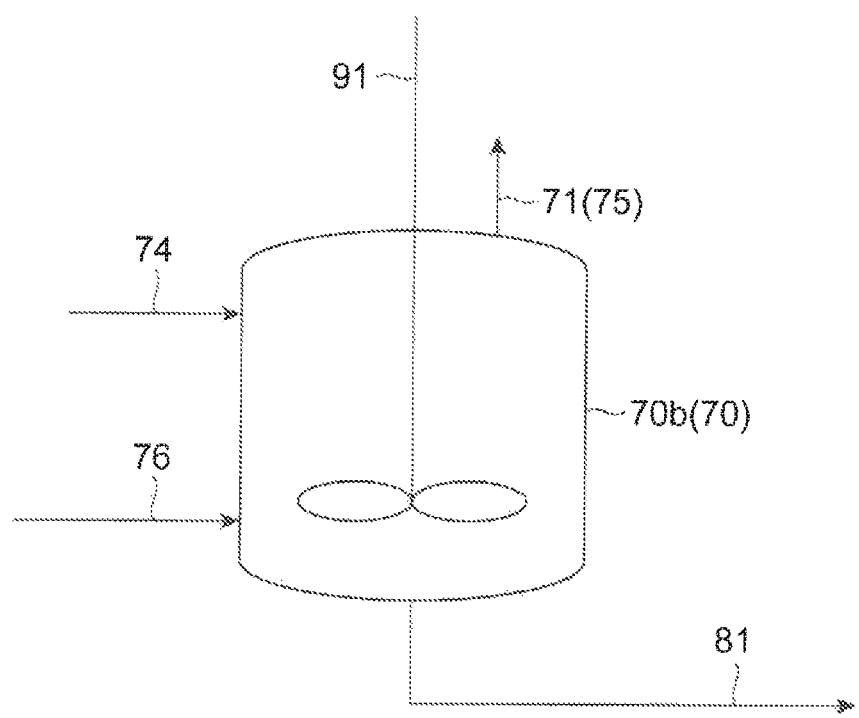
FIG. 18 schematically illustrates another modification of a third reactor in an ester production device according to one embodiment.

FIG. 18 illustrates another modification of the third reactor 70 in the production devices according to the above-described embodiments. The third reactor 70b in FIG. 18 is a stirring tank. To the third reactor 70b, the bottom liquid in the second reactor 30 is fed from the passage 74, and the noncondensable gas is fed from the passage 76. The third reactor 70b includes a stirrer 91 including a rotation shaft and blades attached to the tip of the rotation shaft. The stirrer 91 rotates around the rotation shaft to mix the bottom liquid and the noncondensable gas in the third reactor 70b together. The noncondensable gas may be introduced into the bottom liquid stagnating in the bottom of the third reactor 70b for bubbling.

If the stirring speed of the stirrer 91 is increased, the reactions represented by the above formula (5) and formula (6) are accelerated to increase the amount of a nitrite ester formed. Thus, the concentration of a nitrite ester in the first gas and the third gas can be increased. The fourth gas discharged from the upper part of the third reactor 70b and containing a nitrite ester flows through the passage 71 or the passage 75, and then is fed to the second reactor 30.

Figure 19:
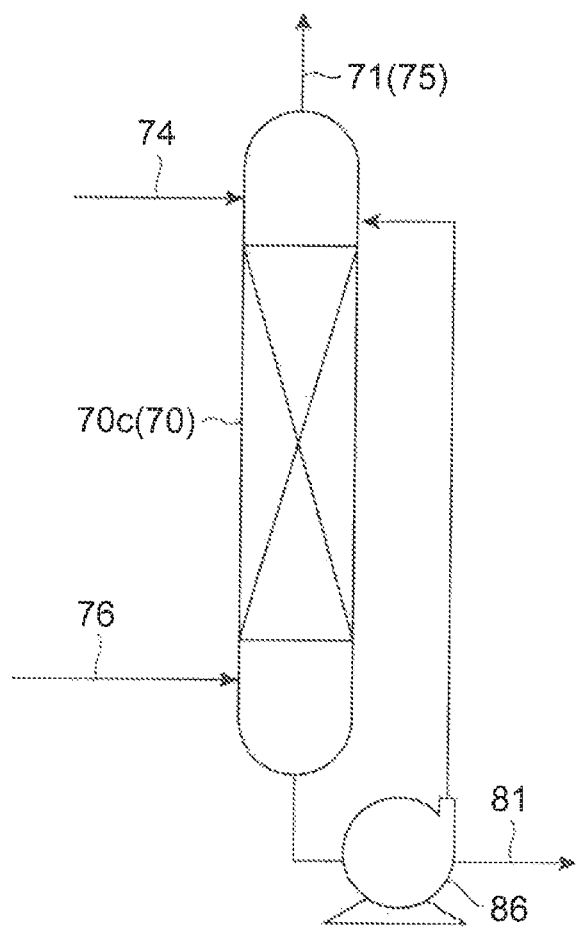
FIG. 19 schematically illustrates still another modification of a third reactor in an ester production device according to one embodiment.

FIG. 19 illustrates still another modification of the third reactor 70 in the production devices according to the above-described embodiments. The third reactor 70c in FIG. 19 is a circulation column. To the third reactor 70c, the bottom liquid in the second reactor 30 is fed from the passage 74, and the noncondensable gas is fed from the passage 76. From the bottom of the third reactor 70c, the bottom liquid is discharged through the passage 81. A part of the bottom liquid to be discharged is circulated to the upper part of the third reactor 70c with a pump 86 or the like. The bottom liquid circulated and fed from the upper part of the third reactor 70c flows through the passage 76 and is brought into countercurrent contact with the noncondensable gas fed to the lower part of the third reactor 70c.

If the flow rate of the bottom liquid circulated is increased, the reactions represented by the above formula (5) and formula (6) are accelerated to increase the amount of a nitrite ester formed. Thus, the concentration of a nitrite ester in the first gas and the third gas can be increased. The fourth gas discharged from the upper part of the third reactor 70c and containing a nitrite ester flows through the passage 71 or the passage 75, and then is fed to the second reactor 30. The inside of the third reactor 70c may be packed with a packing material to increase the contact area between the bottom liquid flowing downward therein and the noncondensable gas flowing upward therein. The noncondensable gas may be introduced into the bottom liquid stagnating in the bottom of the third reactor 70c for bubbling.

In the above-described embodiments, the carbonate ester is, for example, a dialkyl carbonate. The two alkyl groups in a dialkyl carbonate may be identical or different. Examples of the dialkyl carbonate include dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonyl carbonate, ethyl methyl carbonate, and ethyl propyl carbonate.

Among dialkyl carbonates, dialkyl carbonates having a $C_{1-10}$ linear or branched alkyl group are preferred, and dimethyl carbonate and diethyl carbonate are more preferred, in view of the reaction rate of transesterification reaction and easiness in removal of a by-produced alkyl alcohol.

The carbonate ester may be a diaryl carbonate. A diaryl carbonate can be produced, for example, by using a production method including: reacting a dialkyl oxalate and a phenolic compound such as phenol in the presence of a catalyst to form a diaryl oxalate; subjecting the diaryl oxalate to decarbonylation reaction in the presence of a catalyst to form a diaryl carbonate and carbon monoxide; and separating the diaryl carbonate and carbon monoxide to collect the diaryl carbonate. A known catalyst can be used for the catalyst to be used in each step.

The nitrite ester is a nitrite ester corresponding to a carbonate ester and oxalic ester, and for example, is an alkyl nitrite. Examples of the alkyl nitrite include methyl nitrite, ethyl nitrite, propyl nitrite, isopropyl nitrite, butyl nitrite, pentyl nitrite, hexyl nitrite, heptyl nitrite, octyl nitrite, and nonyl nitrite.

In the above-described embodiments, the oxalic ester is, for example, a dialkyl oxalate. The two alkyl groups in a dialkyl oxalate may be identical or different. Examples of the dialkyl oxalate include dimethyl oxalate, diethyl oxalate, dipropyl oxalate, diisopropyl oxalate, dibutyl oxalate, dipentyl oxalate, dihexyl oxalate, diheptyl oxalate, dioctyl oxalate, dinonyl oxalate, ethyl methyl oxalate, and ethyl propyl oxalate. Among dialkyl oxalates, dialkyl oxalates having a $C_{1-10}$ linear or branched alkyl group are preferred, and dimethyl oxalate and diethyl oxalate are more preferred, in view of the reaction rate of transesterification reaction and easiness in removal of a by-produced alkyl alcohol.

The oxalic ester may be a diaryl oxalate. A diaryl oxalate can be produced, for example, by using a production method including reacting a dialkyl oxalate and a phenolic compound such as phenol in the presence of a catalyst to form a diaryl oxalate. A known catalyst can be used for the catalyst to be used in the step.

An embodiment of the method for producing an ester including at least one of a carbonate ester and an oxalic ester, will be described in the following. The production method according to the present embodiment can be implemented, for example, by using the production device 100, 300. The production method includes the following steps:

(a) a first step of introducing a first gas containing carbon monoxide, a nitrite ester, and nitric oxide into the first reactor 10 and reacting the first gas in the presence of a catalyst to form a second gas containing at least one of a carbonate ester and an oxalic ester and nitric oxide;

(b) a second step of allowing the second gas to contact with an absorbing solution in the absorption column 20 to obtain a condensate containing at least one of a carbonate ester and an oxalic ester and a noncondensable gas containing nitric oxide;

(c) a third step of introducing an alcohol and a mixed gas obtained by mixing the noncondensable gas with oxygen gas into the second reactor 30 and reacting nitric oxide, oxygen, and the alcohol to obtain a third gas containing a nitrite ester together with nitric oxide;

(d) a fourth step of distilling the condensate in the distillation column 60 to obtain at least one of a carbonate ester and an oxalic ester;

(e) a fifth step of mixing the third gas with carbon monoxide to obtain the first gas;

(f) a sixth step of feeding the noncondensable gas and a bottom liquid discharged from the bottom of the second reactor 30 and containing water, nitric acid, and an alcohol to the third reactor 70 to form a nitrite ester and feeding the nitrite ester to the second reactor;

(g) a seventh step of detecting the concentration of a nitrite ester in the first gas and/or the third gas in the first measurement unit 40 and adjusting the amount of the noncondensable gas to feed to the third reactor 70 on the basis of the concentration; and (h) an eighth step of detecting the concentration of nitric oxide in the first gas and/or the third gas and adjusting the amount of oxygen to mix with the noncondensable gas on the basis of the concentration.

The first to eighth steps can be repeated. It is not required to perform the steps in the order presented, and the steps may be performed simultaneously. Each of the steps can be performed on the basis of the content of the description on the production device 100, 300.

A production method according to some other embodiments includes the following ninth step in place of the eighth step. That is, the production method includes the first to seventh steps and the ninth step:

(i) a ninth step of detecting the concentration of nitric oxide in the first gas and/or the third gas and adjusting the amount of nitric acid to feed to the third reactor 70 on the basis of the concentration.

The ninth step can be repeated together with the first to seventh steps. It is not required to perform the steps in the order presented, and the steps may be performed simultaneously. The ninth step can be performed by using the production device 101, and can be performed on the basis of the content of the description on the production device 101. In this case, feeding nitric acid from the nitric acid tank 77 to the third reactor 70 may be included. This step can be also performed on the basis of the content of the description on the production device 101.

A production method according to some still other embodiments includes the following 10th step in place of the eighth step. That is, the production method includes the first to seventh steps and the 10th step:

(j) a 10th step including at least one of detecting the concentration of nitric oxide in the first gas and/or the third gas and adjusting the amount of oxygen to feed to mix with the noncondensable gas on the basis of the concentration, and detecting the concentration of nitric oxide in the first gas and/or the third gas and adjusting the amount of nitric acid to feed to the third reactor 70 on the basis of the concentration.

The 10th step can be repeated together with the first to seventh steps. It is not required to perform the steps in the order presented, and the steps may be performed simultaneously. The 10th step can be performed by using the production device 102, and can be performed on the basis of the content of the description on the production device 102.

A production method according to some still other embodiments includes the following 11th step in place of the sixth step, the seventh step, and the eighth step. The production method includes the first to fifth steps and the 11th step, and can be performed, for example, by using the production device 200:

(h) an 11th step of detecting the concentration of a nitrite ester in the first gas and/or the third gas and adjusting the amount of nitric oxide to feed to mix with the noncondensable gas on the basis of the concentration.

The 11th step can be repeated together with the first to fifth steps. It is not required to perform the steps in the order presented, and the steps may be performed simultaneously. Each of the steps can be performed on the basis of the content of the description on the production device 100, 101, 102, 200, 300.

The production methods according to the above-described embodiments can suppress the variation of the concentration of a nitrite ester and maintain high safety, and simultaneously can suppress lowering of the reaction rate in the first reactor 10 sufficiently. Accordingly, at least one of a carbonate ester and an oxalic ester can be produced stably.

Hereinbefore, some embodiments of the present invention have been described; however, it is needless to say that the present invention is never limited to the above-described embodiments. For example, an ester consisting of only one of a carbonate ester and an oxalic ester may be produced. Alternatively, a carbonate ester and an oxalic ester may be produced simultaneously to obtain an ester consisting of a carbonate ester and an oxalic ester through adjustment of the content ratio between carbon monoxide and a nitrite ester in the first gas and selection of the catalyst in the first reactor 10.

Although the control units 50, 52 automatically control the first flow rate-adjusting unit 72, the second flow rate-adjusting unit 79, the third flow rate-adjusting unit 26, and the fourth flow rate-adjusting unit 21 in the above-described embodiments, the flow rate-adjusting units may be manually adjusted while measurement results of the first measurement unit 40 and the second measurement unit 42 are checked, without providing the control units 50, 52.

The production devices 100, 101, 102, 200, 300 may include a plurality of the second reactors 30. In this case, the first measurement unit 40 and the second measurement unit 42 may be provided in the downstream side of each of the plurality of the second reactors 30. Including a plurality of the second reactors 30 allows shutdown of one second reactor 30 for maintenance while operation with the other second reactor 30 is continued.

INDUSTRIAL APPLICABILITY

The present disclosure can provide a production method enabling stable production of an ester including at least one of a carbonate ester and an oxalic ester. In addition, a production device allowing for stable production of an ester including at least one of a carbonate ester and an oxalic ester can be provided.

REFERENCE SIGNS LIST

10: first reactor, 55: junction part, 20: absorption column, 21: fourth flow rate-adjusting unit, 26: third flow rate-adjusting unit, 30: second reactor, 31: CPU, 32: ROM, 33: RAM, 34: input device, 35: output device, 36: communication module, 37: auxiliary storage, 40: first measurement unit (non-dispersive infrared analyzer), 42: second measurement unit, 43: light source, 44: measurement cell, 45: light chopper, 46: optical filter, 47: comparison cell, 48, 49: transmission window, 50, 52: control unit, 51: detector, 53: thin membrane, 54a: first chamber, 54b: second chamber, 56: fixed electrode, 57: lead, 58: signal processing unit, 60: distillation column, 70, 70a, 70b, 70c: third reactor, 72: first flow rate-adjusting unit, 77: nitric acid tank, 79: second flow rate-adjusting unit, 80: nitric acid-concentrating column, 86: pump, 90: cooler, 91: stirrer, 100, 101, 102, 200, 300: production device

The invention claimed is:

1. A method for producing an ester including at least one of a carbonate ester and an oxalic ester, the method comprising:
    introducing a first gas containing carbon monoxide, a nitrite ester, and nitric oxide into a first reactor and reacting the first gas in a presence of a catalyst to obtain a second gas containing an ester including at least one of a carbonate ester and an oxalic ester and nitric oxide;
    allowing the second gas to contact with an absorbing solution to obtain a condensate containing the ester and a noncondensable gas containing nitric oxide;
    introducing an alcohol and a mixed gas obtained by mixing the noncondensable gas with oxygen gas into a second reactor to obtain a third gas containing a nitrite ester and nitric oxide;
    distilling the condensate to obtain the ester;
    mixing the third gas with carbon monoxide to obtain the first gas;
    feeding the noncondensable gas and a bottom liquid discharged from a bottom of the second reactor and containing water, nitric acid, and an alcohol to a third reactor to form a fourth gas containing a nitrite ester, and feeding the fourth gas to the second reactor; and
    measuring a concentration of a nitrite ester in the first gas and/or the third gas, and at least one of adjusting an amount of the noncondensable gas to feed to the third reactor on a basis of the concentration and adjusting an amount of nitric acid to feed to the third reactor on a basis of the concentration.

2. A method for producing an ester including at least one of a carbonate ester and an oxalic ester, the method comprising:
    introducing a first gas containing carbon monoxide, a nitrite ester, and nitric oxide into a first reactor and reacting the first gas in a presence of a catalyst to obtain a second gas containing an ester including at least one of a carbonate ester and an oxalic ester and nitric oxide;
    allowing the second gas to contact with an absorbing solution to obtain a condensate containing the ester and a noncondensable gas containing nitric oxide;
    introducing an alcohol and a mixed gas obtained by mixing the noncondensable gas with oxygen gas into a second reactor to obtain a third gas containing a nitrite ester and nitric oxide;
    distilling the condensate to obtain the ester;
    mixing the third gas with carbon monoxide to obtain the first gas; and
    measuring a concentration of a nitrite ester in the first gas and/or the third gas and adjusting an amount of nitric oxide to mix with the noncondensable gas on a basis of the concentration.

3. The method according to claim 1, wherein the concentration of a nitrite ester in the first gas and/or the third gas is measured by using non-dispersive infrared analysis.

4. The method according to claim 3, wherein an infrared analyzer including a measurement cell to allow the first gas and/or the third gas to flow therethrough and a detector encapsulating ammonia is used in the non-dispersive infrared analysis.

5. The method according to claim 1, comprising measuring a concentration of nitric oxide in the first gas and/or the third gas and adjusting an amount of the oxygen gas to mix with the noncondensable gas on a basis of the concentration.

6. The method according to claim 1, wherein the concentration of the nitrite ester in the first gas is maintained at 5 to 25% by volume based on a total of the first gas.

7. The method according to claim 1, wherein the concentration of the nitrite ester in the third gas is maintained at 5 to 30% by volume based on a total of the third gas.

8. A device for producing an ester including at least one of a carbonate ester and an oxalic ester, the device comprising:
    a first reactor to react a first gas containing carbon monoxide, a nitrite ester, and nitric oxide in a presence of a catalyst to obtain a second gas containing an ester including at least one of a carbonate ester and an oxalic ester and nitric oxide;
    an absorption column to allow the second gas to contact with an absorbing solution to separate into a condensate containing the ester and a noncondensable gas containing nitric oxide;
    a second reactor to introduce an alcohol and a mixed gas containing the noncondensable gas and oxygen gas thereinto to obtain a third gas containing a nitrite ester and nitric oxide;
    a distillation column to distill the condensate to obtain the ester;
    a junction part to allow the third gas and carbon monoxide to join together to obtain the first gas;
    a third reactor to form a fourth gas containing a nitrite ester from the noncondensable gas and a bottom liquid discharged from a bottom of the second reactor and containing water, nitric acid, and an alcohol and to feed the fourth gas to the second reactor;
    a first measurement unit to measure a concentration of a nitrite ester in the first gas and/or the third gas; and
    at least one of a first flow rate-adjusting unit to adjust an amount of the noncondensable gas to feed to the third reactor on a basis of the concentration, and a second flow rate-adjusting unit to adjust an amount of nitric acid to feed to the third reactor on a basis of the concentration.

9. A device for producing an ester including at least one of a carbonate ester and an oxalic ester, the device comprising:
- a first reactor to react a first gas containing carbon monoxide, a nitrite ester, and nitric oxide in a presence of a catalyst to obtain a second gas containing an ester including at least one of a carbonate ester and an oxalic ester and nitric oxide;
- an absorption column to allow the second gas to contact with an absorbing solution to separate into a condensate containing the ester and a noncondensable gas containing nitric oxide;
- a second reactor to introduce an alcohol and a mixed gas containing the noncondensable gas and oxygen gas thereinto to form a third gas containing a nitrite ester and nitric oxide;
- a distillation column to distill the condensate to obtain the ester;
- a junction part to allow the third gas and carbon monoxide to join together to obtain the first gas;
- a first measurement unit to measure a concentration of a nitrite ester in the first gas and/or the third gas; and
- a third flow rate-adjusting unit to adjust an amount of nitric oxide to mix with the noncondensable gas on a basis of the concentration.

10. The device according to claim 8, comprising a control unit to control at least one of the first flow rate-adjusting unit and the second flow rate-adjusting unit so that the concentration of a nitrite ester in the first gas becomes 5 to 25% by volume based on a total of the first gas.

11. The device according to claim 8, comprising a control unit to control at least one of the first flow rate-adjusting unit and the second flow rate-adjusting unit so that the concentration of a nitrite ester in the third gas becomes 5 to 30% by volume based on a total of the third gas.

12. The device according to claim 9, comprising a control unit to control the third flow rate-adjusting unit so that the concentration of a nitrite ester in the first gas becomes 5 to 25% by volume based on a total of the first gas.

13. The device according to claim 9, comprising a control unit to control the third flow rate-adjusting unit so that the concentration of a nitrite ester in the third gas becomes 5 to 30% by volume based on a total of the third gas.

14. The device according to claim 8, wherein the first measurement unit includes a non-dispersive infrared analyzer.

15. The device according to claim 14, wherein the non-dispersive infrared analyzer includes a measurement cell to allow the first gas and/or the third gas to flow therethrough, and a detector encapsulating ammonia.

16. The device according to claim 8, comprising:
- a second measurement unit to measure a concentration of nitric oxide in the first gas and/or the third gas; and
- a fourth flow rate-adjusting unit to adjust an amount of the oxygen gas to mix with the noncondensable gas on a basis of the concentration.

17. The method according to claim 2, wherein the concentration of a nitrite ester in the first gas and/or the third gas is measured by using non-dispersive infrared analysis.

18. The method according to claim 17, wherein an infrared analyzer including a measurement cell to allow the first gas and/or the third gas to flow therethrough and a detector encapsulating ammonia is used in the non-dispersive infrared analysis.

19. The device according to claim 9, wherein the first measurement unit includes a non-dispersive infrared analyzer.

20. The device according to claim 19, wherein the non-dispersive infrared analyzer includes a measurement cell to allow the first gas and/or the third gas to flow therethrough, and a detector encapsulating ammonia.

* * * * *